United States Patent
Cozens et al.

(10) Patent No.: US 6,995,221 B2
(45) Date of Patent: Feb. 7, 2006

(54) METHOD FOR PRODUCING ORGANIC PEROXIDES AND THEIR USE IN THE RADICAL POLYMERIZATION OF MONOMERS

(75) Inventors: Ross J. Cozens, Strongsville, OH (US); Qi Wang, Birdsboro, PA (US); M. Frederick V. Glock, Jr., Richfield, OH (US); Daniel A. Zust, Avon, OH (US)

(73) Assignee: Oxy Vinyls, L.P., Dallas, TX (US)

( * ) Notice: Subject to any disclaimer, the term of this patent is extended or adjusted under 35 U.S.C. 154(b) by 217 days.

(21) Appl. No.: 10/430,719

(22) Filed: May 6, 2003

(65) Prior Publication Data

US 2004/0249097 A1 Dec. 9, 2004

Related U.S. Application Data

(60) Continuation-in-part of application No. 10/132,582, filed on Apr. 25, 2002, now Pat. No. 6,770,719, which is a division of application No. 09/433,907, filed on Nov. 4, 1999, now Pat. No. 6,433,208.

(51) Int. Cl.
*C08F 4/28* (2006.01)

(52) U.S. Cl. .................... 526/227; 526/237; 526/344.2; 526/230.5; 526/230; 526/229; 526/228; 526/232.1; 526/932; 526/910; 526/911

(58) Field of Classification Search ................. 526/227, 526/230, 237, 228, 229, 232.1, 344.2, 932, 526/911, 910, 230.5
See application file for complete search history.

(56) References Cited

U.S. PATENT DOCUMENTS 6,258,906 B1 * 7/2001 Bodart ........................ 526/227

\* cited by examiner

*Primary Examiner*—William K. Cheung
(74) *Attorney, Agent, or Firm*—T. Dean Simons

(57) ABSTRACT

A process for producing organic peroxide initiators useful in the polymerization of ethylenically unsaturated monomers. The process for making the organic peroxides includes forming an aqueous emulsion of the organic peroxide. The organic peroxide is dispersed as small droplets of from 1 to 10 microns in size in the aqueous emulsion. The organic peroxide may be added to a polymerization reactor containing an ethylenically unsaturated monomer. The organic peroxide functions as a free radical initiator to polymerize the monomer. The organic peroxide may be substantially free of organic solvents and plasticizers. The resulting polymers are of high quality.

32 Claims, No Drawings

US 6,995,221 B2

METHOD FOR PRODUCING ORGANIC PEROXIDES AND THEIR USE IN THE RADICAL POLYMERIZATION OF MONOMERS

This application claims the benefit of and is a Continuation-in-Part of regular U.S. patent application Ser. No. 10/132,582 filed Apr. 25, 2002, now U.S. Pat. No. 6,770,719 which is a divisional application of regular U.S. patent application Ser. No. 09/433,907 filed Nov. 4, 1999 and now issued as U.S. Pat. No. 6,433,208.

BACKGROUND OF THE INVENTION

Organic peroxides are important for use as free radical producing initiators in the polymerization field, and particularly in the polymerization of ethylenically unsaturated monomers, such as vinyl chloride. There are numerous classes of organic peroxides. Commercially important classes of organic peroxides are dialkyl peroxides, diacyl peroxides, peroxydicarbonates, and peroxyesters.

A frequently employed industrial method for the synthesis of dialkyl peroxides is the alkylation of hydroperoxides with alcohols, olefins, esters, halides or epoxides (*Ullmann's Encyclopedia of Industrial Chemistry*, $4^{th}$ ed., VCH, 1991, Vol. 19, pp. 205, J. Sanchez' T. N. Myers, in *Kirk-Othmer Encyclopedia of Industrial Technology*, $4^{th}$ ed., Wiley, 1996, pp.248–252). Reaction conditions depend on the nature of the reactants and usually involve acid or base catalysis. A typical industrial method for the synthesis of diacyl peroxides is the reaction of acyl halides or carboxylic acid anhydrides with hydrogen peroxide or an alkali metal peroxide (*Ullmann's Encyclopedia of Industrial Chemistry*, $4^{th}$ ed, 1991, Vol 19, pp. 211–212; J. Sanchez, T. N. Myers, *Kirk-Othmer Encyclopedia of Industrial Technology*, $4^{th}$ ed., Wiley, 1996, pp. 280–283).

An important industrial method for the synthesis of organic peroxyesters is the reaction of carboxylic acid halides, particularly chloride, with hydroperoxides. (In *Ullmann's Encyclopedia of Industrial Chemistry*, $4^{th}$ ed. VCH, 1991, Vol. 19, pp. 216.) The process is usually carried out with high selectivity under Schotten-Baumann conditions using either organic or inorganic bases in aqueous or aqueous-organic media. Batch processing is generally employed when relatively small production volumes are required, whereas semi-continuous and continuous processing are employed when larger production volumes are required and when safety is a primary issue. (J. Sanchez; T. N. Myers, in *Kirk-Othmer Encyclopedia of Industrial Technology*, $4^{th}$ ed. Wiley, 1996, Vol. 18, pp. 292–293; P. M. Kohn, *Chem. Eng.* 1978, July 17, 88–89; U.S. Pat. No. 4,075,236.) In the case of preparing the peroxyesters in aqueous-organic media using aqueous alkali, phase transfer catalysis was developed to speed up the reaction at lower temperature. (S. Baj; A Chrobok; *Polish J. Chem.* 1999, 73, 1185–1189.)

Organic peroxides are typically made in large batches and sold in pure form, either as neat or diluted products. Polymer producers must store large quantities of organic peroxides for use in their polymerization processes. Precautions must be taken with the storage and handling of these materials as they are unstable and are sensitive to both thermal and impact shock and can detonate under certain conditions. Complying with all of the safety requirements of handling these materials results in the organic peroxides being very expensive to employ in the manufacture of polymers.

Various solutions to this problem have been proposed in the past. U.S. Pat. No. 4,359,427 proposes a process to continuously produce and purify peroxydicarbonates on the polymerization site and to store them in a diluted phase until used. Another approach that has been suggested is to produce organic peroxides in a large polymerization vessel before adding the polymerizable monomer. This is sometimes referred to as in-situ synthesis. Making the organic peroxide in a large vessel has resulted in quality problems for the polymer being produced for several reasons. One such reason is that there is not adequate mixing of the small amount of reactants in a large reactor vessel. Without adequate mixing, the reaction to form the organic peroxide is inefficient and the yield of organic peroxide produced varies, thus making the polymerization reactions using the organic peroxide initiators vary in reaction times. To make greater volumes, diluents are often used, such as solvents and water. With these diluents there is poor conversion of the reactants resulting in large amounts of undesirable by-products which are formed and which remain in the large reactor to contaminate the polymer that is ultimately produced in the reactor. Solvent dilution results in solvent being present which must be recovered and contaminates the recovery system for recovering unreacted monomer. Also, by making the organic peroxides in large polymerization vessels, productivity is lowered because the polymerization vessel is occupied with the organic peroxide synthesis process before each batch of polymer can be produced.

Great Britain Patent 1,484,675 proposes to solve these problems by producing peroxydicarbonates outside of the polymerization vessel in the presence of a solvent to obtain adequate mixing of the reactants. This method is undesirable because the solvent must be removed or else it becomes a contaminant in the polymerization process and contaminates the polymerization process monomer recovery system.

WO 97/27229 patent application proposes to solve the problem by making peroxydicarbonates outside of the polymerization reactor in a two-step process and adding a water insoluble liquid dialkyl alkanedicarboxylate. The dialkyl alkane dicarboxylate is a plasticizer for the resulting polymer and is undesirable in rigid applications of the polymer. Also, the two-step process is cumbersome and requires excess equipment.

U.S. Pat. No. 4,359,427, Great Britain patent 1,484,675 and WO 97/27229 all teach that peroxydicarbonates can be produced by reacting a chloroformate with an alkali metal peroxide.

U.S. Pat. No. 5,962,746 discloses production of organic peroxides by reacting a hydroxide, a peroxide, and an acyl halide under continuous vigorous agitation conditions. For example, disclosed is the batch-wise synthesis of diisobutyryl peroxide from isobutyryl chloride and either (1) ammonium hydroxide and hydrogen peroxide or (2) potassium hydroxide and hydrogen peroxide, using high power ultrasonication over a short reaction time in a hexane-water medium. These methods produced diisobutyryl peroxide in relatively low yields of 47% and 29% respectively.

The synthesis of diisobutyryl peroxide on a batch-wise basis from isobutyryl chloride and sodium peroxide using a magnetically stirred, two-phase reaction mixture at 25–30° C. was reported in M. Ravey, J. Poly. Sci. Poly. Chem. Ed., 15 1977, pp. 2559–2570. This disclosure reports that low yields of product (approximately 50%) only were achieved, and the reduced yield was attributed to hydrolysis of the isobutyryl chloride under the reaction conditions.

The in-situ synthesis of diisobutyryl peroxide on a batch-wise basis from isobutyric anhydride in mechanically tumbled reactors, with yields of around 67% was reported in J. A. Barter, D. E. Kellar, J. Poly. Sci. Poly. Chem. Ed., 15, 1977, pp. 2545–2557. Under more concentrated conditions, in a two-phase reaction system, isobutyryl chloride in hexane was slowly added to an aqueous solution of sodium peroxide, followed by a short period of rapid agitation, resulting in yields of diisobutyryl peroxide of around 72%. The use of isobutyryl chloride as a starting material under in-situ reaction conditions resulted in very low yields of the desired diisobutyryl peroxide.

SUMMARY OF THE INVENTION

It has been unexpectedly found that organic peroxide initiators can be produced at high yield and sufficient purity outside of a polymerization vessel, at an industrial polymerization site or other appropriate location. The peroxides are useful for polymerizing ethylenically unsaturated monomers to yield high quality polymers. The organic peroxides are produced in the form of an aqueous emulsion by contacting reactants under conditions of agitation in the presence of a dispersant.

DETAILED DESCRIPTION

Organic peroxides, which are used widely as free radical initiators in industrial scale polymerization processes, are inherently unstable, making them difficult to produce and store, especially at industrial polymerization sites. It has been unexpectedly determined that stable organic peroxides may be produced outside of polymerization reactors, at industrial polymerization sites, through the use of certain emulsions. Reactants for production of a selected organic peroxide are contacted under conditions of agitation in the presence of a dispersant to produce an emulsion of the reactants. As the peroxide producing reaction proceeds, an emulsion of reactants converts to the selected peroxide. It is found that the peroxide is produced in high yields and the peroxide emulsion is usually stable and of high purity.

It is found that creation of the emulsion of reactants contributes to faster peroxide producing reaction rates leading to higher yields. The resulting stable peroxide emulsions are found to be beneficial for production of high quality polymers when used as free radical initiators by producing unusually uniform polymer products.

Organic peroxides will be discussed and exemplified by reference to diakyl peroxides, diacyl peroxides, peroxydicarbonates, and peroxyesters.

Dialkyl and Diacyl Peroxides

The processes for making the dialkyl and diacyl peroxides described herein involve forming a mixture of at least one peroxide, preferably an inorganic peroxide, and an aqueous emulsion of at least one organic halide wherein the emulsion is comprised of droplets of the organic halide with diameters of less than 10 μm. The mixture of the at least one inorganic peroxide and the aqueous emulsion reacts to form an aqueous emulsion of the desired dialkyl or diacyl peroxide.

Dialkyl and diacyl peroxides produced by this invention have the following formula:

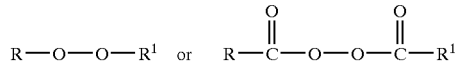

where R and $R^1$ are different or identical organic radicals having from 2 to 16 carbon atoms in one embodiment, 2 to 10 carbon atoms in another embodiment, and 2 to 6 carbon atoms in still another embodiment. In one embodiment, the dialkyl and diacyl peroxides have R and $R^1$ as identical radicals. Specific examples of R and $R^1$ are alkyl radicals such as ethyl, n-propyl, isopropyl, n-butyl, isobutyl, isobutyryl, secondary butyl, amyl, hexyl or 2-ethylhexyl; alkenyl, aryl, alkylaryl, arylalkyl or cycloakyl radicals, or radicals derived from heterocyclic compounds and, particularly radicals such as benzyl, cyclohexyl, cinnamyl, tetrahydrofuryl, and also their substituted derivatives. In one embodiment, exemplary dialkyl peroxides are di-tert-butyl peroxide and dicumyl peroxide. In another embodiment, exemplary diacyl peroxides are diisobutyryl peroxide, dilauroyl peroxide and dibenzoyl peroxide.

The organic halides used to produce the dialkyl and diacyl peroxides have the general formula:

wherein $R^2$ is an organic radical containing from 2 to 16 carbon atoms. $R^2$ is the same organic radical as described above for R and $R^1$. $R^3$ is a halogen, such as chlorine, fluorine, iodine or bromine. In one embodiment, $R^3$ is chlorine. One or more than one organic halide may be used to produce the organic peroxide.

At least one dispersant is used in the synthesis of the dialkyl and diacyl peroxides. Dispersants such as hydrolyzed polyvinyl acetates, alkyl and hydroxyalkyl cellulose ethers such as methyl cellulose or hydroxypropyl methyl cellulose, gelatin, polyvinylpyrrolidone, polyoxyethlyene sorbitan monolaurate, polyacrylic acid and like compounds may be used and mixtures thereof. In one embodiment, the dispersant is selected to be similar to the dispersant used in the polymerization of the ethylenically unsaturated monomer for which the peroxide may be used as an initiator. For polymerizing vinyl chloride monomer, in one embodiment the dispersant is hydrolyzed polyvinyl acetate having a hydrolysis in the range of about 70% to about 90%. In one embodiment, the dispersant is preferably added as a water solution. The level of dispersant used should be sufficient to form a water emulsion of the alkyl or acyl halide. In one embodiment, this level is from about 0.05 to 0.2 gram of dispersant per gram of alkyl or acyl halide. In another embodiment, the level is from about 0.075 to about 0.1 gram of dispersant per gram of alkyl or acyl halide.

In one embodiment, the alkyl or acyl halide emulsion has the alkyl or acyl halide droplets having a diameter less than about 10 microns, and less than about 5 microns in another embodiment, and from about 1 to about 4 microns in still another embodiment. The small droplet size of alkyl or acyl halide in the emulsion is advantageous for high reaction rates and high yields in production of the organic peroxides.

The dispersant is added as a water solution. In one embodiment, the solution has from about 1% to about 10% by weight of dispersant in water, and in another embodiment, from about 3% to about 8% by weight of dispersant in water.

Water is also used in the synthesis of the dialkyl and diacyl peroxides of this invention. The water is required to dissolve the dispersant and dilute other reaction ingredients. Water also assists in removal of the heat resulting from the exothermic reaction. A useful water is demineralized water. The amount of water used is not critical, but it must be sufficient to dissolve the dispersant, the alkali metal hydroxide and the inorganic peroxide. The alkali metal hydroxide and inorganic peroxide are used as aqueous solutions and thus provide a portion of the required water. A minimum amount of water should be used to obtain the required cooling. An excess of water, over that required to dilute the reactants and provide cooling, should be avoided during the reaction so as to give more intimate contact of the reactants.

Once the reaction is complete, additional water may be added, if desired. In one embodiment, the amount of water used to disperse the alkyl or acyl halide is from about 1 gram to about 15 grams of water per gram of alkyl or acyl halide. In another embodiment, from about 3 grams to about 8 grams of water per gram of alkyl or acyl halide is used. Since water is added with the solutions of other ingredients, in one embodiment, the final emulsion of dialkyl or diacyl peroxide will contain from about 2 grams to about 20 grams of water per gram of alkyl or acyl peroxide. In another embodiment, the final emulsion comprises from about 4 grams to about 12 grams of water per gram of alkyl or aryl peroxide.

At least one inorganic peroxide which is typically an alkali metal peroxide is used in the synthesis of the dialkyl and diacyl peroxides of this invention. In one embodiment, the alkali metal peroxide is sodium peroxide. The alkali peroxide may be formed from reacting an inorganic peroxide such as hydrogen peroxide with an alkali metal hydroxide, such as sodium hydroxide, potassium hydroxide, ammonia hydroxide, lithium hydroxide, calcium hydroxide, magnesium hydroxide and alkali metal phosphates. Sodium peroxide is formed by reacting sodium hydroxide with hydrogen peroxide. Two moles of alkali metal hydroxide are used for every one mole of inorganic peroxide. An excess of either reactant can be used, but typically this will not lead to optimal results.

Formation of the inorganic peroxide is described herein in connection with the process for production of the organic peroxide because the inorganic peroxides are very unstable and are typically produced in connection with formation of the organic peroxides. However, it is understood that the processes described herein may be practiced with an inorganic peroxide available from any suitable source.

In one embodiment, the dialkyl and diacyl peroxides are produced using two reaction vessels. The reaction vessels may be of any shape and material, but the shape and material of construction should be conducive to being cooled and chemically compatible with the reaction materials. Metal vessels such as stainless steel pots or pipes are satisfactory. In one vessel, the alkali metal peroxide is produced by mixing the alkali metal hydroxide with inorganic peroxide. The mixture of the alkali metal hydroxide and inorganic peroxide are thoroughly mixed by conventional mechanical agitation to form the alkali metal peroxide. In one embodiment, sodium hydroxide is mixed with hydrogen peroxide to produce sodium peroxide. The preferred sodium hydroxide used is a water solution of sodium hydroxide. The concentration of sodium hydroxide is not critical but, in one embodiment, the concentration ranges from about 5 wt. % to about 35 wt. % percent solution of sodium hydroxide in water, and in another embodiment, the concentration ranges from about 5 wt. % to about 20 wt. % of sodium hydroxide in the solution. In one embodiment, the hydrogen peroxide used is a 5% to 35 weight % solution of hydrogen peroxide in water.

The mixture used to make the alkali metal peroxide may vary considerably. However, the ratio of alkali metal hydroxide to inorganic peroxide should be at least 2:1. In order to achieve stoichiometric efficiency, in one embodiment, two moles of alkali metal hydroxide should be mixed with every one mole of inorganic peroxide. The reversible reaction can be shown for exemplary reactants as:

$$2NaOH + H_2O_2 \leftrightarrows Na_2O_2 + 2H_2O$$

The temperature of the reaction should be maintained below the decomposition temperature of the alkali metal peroxide. Also, the mixture may be cooled so as not to add heat when later used to make the dialkyl or diacyl peroxide.

In one embodiment, the alkali metal peroxide is cooled to less than 28° C. and in another embodiment, to a temperature of from 0° C. to 10° C.

In this embodiment, the second vessel is equipped with a homogenizer apparatus and cooling means, and the alkyl or acyl halide, dispersant and water are added. The mixture of alkyl or acyl halide, dispersant and water is cooled and homogenized while adding the alkali metal peroxide from the first vessel. In one embodiment, the homogenization is started before the alkali metal peroxide is added and continues until all of the alkali metal peroxide has been added. The temperature of the mixture of the second vessel should be maintained below the decomposition temperature of the dialkyl or diacyl peroxide to be formed. In one embodiment, the temperature should be maintained below 40° C., in another embodiment, below 22° C. and still another embodiment, from 0° C. to 10° C. Because water is present, the temperature of the mixture should be maintained high enough to avoid freezing the water, although the freezing temperature of the water in the mixture is lower than 0° C. because of the presence of by-products including salts. If the temperature is above the decomposition temperature of the dialkyl or diacyl peroxide formed, efficiency is lowered as the dialkyl or diacyl peroxide will decompose. Decomposition can be observed by foaming caused by the liberation of oxygen or carbon dioxide when the dialkyl or diacyl peroxide decomposes. The alkali metal peroxide can be added to the second vessel at a rate which is determined by the ability to cool the second vessel, such as not to exceed the decomposition temperature of the dialkyl or diacyl peroxide formed. The reaction of the alkali metal peroxide and alkyl or acyl halide is almost instantaneous and extremely exothermic. Because of the highly exothermic reaction, it is preferred to meter the alkali metal peroxide from the first vessel to the second vessel containing the alkyl or acyl halide over a period of from about 2 to about 20 minutes. The rate of addition of the alkali metal peroxide is dependent only on the ability to cool the reaction, such as to maintain the reaction temperature below the decomposition temperature of the dialkyl or diacyl peroxide being formed.

The alkyl or acyl halide, dispersant and water mixture of the second vessel could be added to the first vessel containing the alkali metal peroxide but this method is less efficient in that yields of dialkyl or diacyl peroxides are lower.

The levels of reactants used in the second vessel may vary considerably. However, the ratio of alkali metal peroxide to alkyl or acyl halide should be at least 2:1. In order to achieve stoichiometric efficiency, in one embodiment, one mole of alkali metal peroxide for every two moles of alkyl or acyl halide is used. The reaction can be shown as follows for diakyl synthesis:

$$Na_2O_2 + 2RCl \rightarrow R\text{—}O\text{—}O\text{—}R + 2NaCl$$

wherein R is tert-butyl (in the case of a specific dialkyl peroxide) or for diacyl synthesis as:

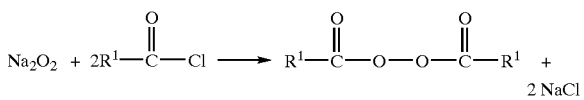

wherein $R^1$ is an isobutyryl group (in the case of a specific diacyl peroxide).

Homogenization of the reactants in the second vessel provides intimate contact between the reactants, resulting in the need to use less reactants. By using less reactants, the need to dilute the reaction with a solvent or a plasticizer is reduced or eliminated, resulting in less by-products which are harmful in the polymerization process of the ethylenically unsaturated monomer. The homogenization also gives dialkyl or diacyl peroxide droplets having diameters less than 10 microns in one embodiment, and less than 5 microns in another embodiment and from 1 to 4 microns in still another embodiment. The small droplet size of the dialkyl or diacyl peroxide is advantageous in producing polymers having low levels of gels.

The type of homogenizer apparatus found to be suitable for larger scale reactions in this invention is a rotor-stator design such as an Arde Barinco™ homogenizer. This type of homogenizer apparatus has a shaft extending into the reactants of the second vessel. The shaft end has narrow slits (teeth) in the fixed stator with a rotating disc having teeth offset from the teeth in the stator, such that the reactants are drawn into and repeatedly cycled through the narrow slits in the stator. For small scale laboratory reactions, a homogenizer of the tissue tearer type such as ESGE Model M-133/1281-0 may be employed.

The reaction in the second vessel to produce the dialkyl or diacyl peroxide should typically be completed just prior to when it is needed in the polymerization cycle. Should there be an unplanned delay in using the dialkyl or diacyl peroxide, the aqueous mixture in the second vessel containing the dialkyl or diacyl peroxide should be agitated. In one embodiment, a simple agitation is used rather than continuing to run the homogenizer, since the homogenizer will undesirably add heat to the aqueous dispersion of the dialkyl or diacyl peroxide. Any type of system for the agitation is acceptable, such as a shaft with blades or a method to bubble inert gas into the vessel, as long as the dialkyl or diacyl peroxide is not allowed to settle on the bottom of the vessel.

Another embodiment to make the dialkyl and diacyl peroxide free radical initiator is to use a continuous mixing process with an in line homogenizer. When using an in-line homogenizer, the alkyl or acyl halide, dispersant and water are injected into a line, such as a pipe. The pipe is connected to a homogenizer. An alkali metal peroxide may be metered into the line just prior to the homogenizer, or preferably after the homogenizer. Suitable in-line homogenizers are those sold by Manton Gaulin, by IKA under the DISPAX line of products and Arde-Barinco under the CAVITRON product line. The ingredients to be homogenized can be passed through the homogenizer multiple times until the desired homogenization is obtained, but are preferably homogenized suitably in one pass. In one embodiment for making dialkyl and diacyl peroxides, sufficient homogenization should be performed to give a droplet size of the dialkyl or diacyl peroxide of from about 1 to 10 microns, and in another embodiment, from about 1 to about 4 microns.

In one embodiment, the emulsion of alkyl or acyl halide is reacted to form the dialkyl and diacyl peroxide by continuously blending alkali metal peroxide solution into the stable emulsion stream with mild mixing in cooled piping or plug flow heat exchanger using the natural turbulent flow in these components. A device known in the art as a static mixer.

In another embodiment, the dialkyl or diacyl peroxide may be formed by adding the inorganic peroxide solution and alkali metal hydroxide solutions separately to an alkyl or acyl halide emulsion. In this case, it is advantageous to add the alkali metal hydroxide last to avoid undesirable hydrolysis of the alkyl or acyl halide. All streams are metered together in the selected ratio and pass in plug flow through a cooler and piping train to remove heat of reaction and provide sufficient residence time for the synthesis reaction to go to completion, typically less than 30 minutes. The line where the dialkyl and diacyl peroxides are formed may be connected directly to the polymerization reactor, and the dialkyl or diacyl peroxide delivered to the reactor at the desired time, or the line may be connected to one or more chilled, agitated storage tanks where the dialkyl or diacyl peroxide may be stored for future use.

If it is desired to produce more than one dialkyl or diacyl peroxide for use in a polymerization, then the reaction to form the first dialkyl or diacyl peroxide should be completed before adding the second alkyl or acyl halide and the corresponding alkali metal peroxide. If two different alkyl or acyl halides are mixed and one alkali metal peroxide is added, three different types of dialkyl and diacyl peroxides will be formed. Two types will be symmetrical with the same end groups on each side, while the third type will have a different end group on each side. Although this type of dialkyl or diacyl peroxide mixture would function as an initiator for polymerization, typically it is not the most desirable mixture. The specific amounts of each of the three different types of dialkyl and diacyl peroxides formed is difficult to control and can vary from batch to batch. For this reason, it is preferred to complete the reaction of the first alkyl or acyl halide before beginning the reaction to form a second dialkyl or diacyl peroxide. Should a third or subsequent dialkyl or diacyl peroxide be desired, then the reaction to complete the second dialkyl or diacyl peroxide should be completed before adding the haloformate to produce the third dialkyl or diacyl peroxide and so forth for each additional desired dialkyl or diacyl peroxide. The synthesis of a dialkyl or diacyl peroxide can precede or follow the synthesis of another organic peroxide to develop an optimized mix of organic peroxides for the kinetically efficient polymerization of a given ethylenically unsaturated monomer.

Various dialkyl and diacyl peroxides can be made by the processes described. The nature, or structure of the initiator produced will depend upon the particular alkyl or acyl halide employed in the reaction.

Peroxydicarbonates

One peroxydicarbonate production embodiment includes first mixing an alkali metal hydroxide with a peroxide to form an alkali metal peroxide. The alkali metal peroxide is added to a mixture of haloformate, dispersant and water to form the desired peroxydicarbonate. The reaction mixture is homogenized during the reaction to give small droplets of peroxydicarbonates. The resulting peroxydicarbonates do not need to be diluted with solvents or plasticizer nor do they need to be purified. The resulting peroxydicarbonates may be produced immediately prior to a polymerization reaction and charged to the polymerization vessel and the polymerization reaction is conducted to give a high quality polymer from the ethylenically unsaturated monomer.

Peroxydicarbonates produced by an embodiment of this invention have the general formula:

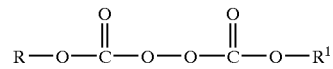

$R$ and $R^1$ are different or identical organic radicals having from 2 to 16 carbon atoms, preferably 2 to 10 carbon atoms, and more preferably from 2 to 6 carbon atoms. The most preferred peroxydicarbonates have R and $R^1$ as identical radicals. Specific examples of R and $R^1$ are alkyl radicals such as ethyl, n-propyl, isopropyl, n-butyl, isobutyl, secondary butyl, amyl, hexyl or 2-ethylhexyl; alkenyl, aryl, alkylaryl, arylalkyl or cycloakyl radicals, or radicals derived from heterocyclic compounds and, particularly radicals such as benzyl, cyclohexyl, cinnamyl, tetrahydrofuryl, and also their substituted derivatives. The most preferred peroxydicarbonates are diethyl peroxydicarbonate, di-n-propyl peroxydicarbonate, di-isopropyl peroxydicarbonate, di-n-butyl peroxydicarbonate, di(secondary butyl) peroxydicarbonate and di(2-ethyl hexyl) peroxydicarbonate.

The haloformates used to produce the peroxydicarbonates have the general formula:

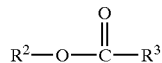

wherein $R^2$ is an organic radical containing from 2 to 16 carbon atoms and $R^3$ is a halogen atom. $R^2$ is the same organic radical as described above for R and $R^1$. $R^3$ is a halogen, such as chlorine, fluorine, iodine or bromine. In one embodiment $R^3$ is chlorine. One or more than one haloformate may be used to produce the peroxydicarbonate.

At least one dispersant is used in the synthesis of the peroxydicarbonate such as hydrolyzed polyvinyl acetates, alkyl and hydroxyalkyl cellulose ethers such as methyl cellulose, hydroxypropyl methyl cellulose, gelatin, polyvinylpyrrolidone, polyoxyethlyene sorbitan monolaurate, polyacrylic acid and like compounds. The dispersant is preferably selected to be similar to the dispersant used in the polymerization of the ethylenically unsaturated monomer. For polymerizing vinyl chloride monomers, the preferred dispersant in hydrolyzed polyvinyl acetate having a hydrolysis in the range of about 70% to about 90%. The dispersant is preferably added as a water solution. The level of dispersant used should be sufficient to form a water emulsion of the haloformate. This level is normally from about 0.05 to 0.2 gram of dispersant per gram of haloformate, preferably from about 0.075 to about 0.1 gram of dispersant per gram of haloformate. The dispersant is added as a water solution. The solution has from about 1% to about 10% by weight of dispersant in water, preferably from about 3% to about 8% by weight of dispersant in water. Once the reaction to form the peroxydicarbonate is complete, additional dispersant may be added to stabilize the emulsion. Stabilizing the emulsion is particularly important if the peroxydicarbonate is not used shortly after being made.

Water is also used in the synthesis of peroxydicarbonates of this invention. The water is required to disperse the dispersant and other reaction ingredients. Water also assists in removal of the heat resulting from the exothermic reaction. Preferably the water used is demineralized water. The amount of water used is not critical except that the amount necessary to disperse the dispersant and dissolve the alkali metal hydroxide and peroxide must be used. The alkali metal hydroxide and peroxide are used as aqueous solutions and thus provide a portion of the required water. Preferably a minimum amount of water is used to get the required cooling. An excess of water, over that required to disperse the reactants and provide cooling, should be avoided during the reaction so as to give more intimate contact of the reactants. Once the reaction is complete, additional water may be added. Normally the amount of water used for the reaction is from about 5 grams to about 20 grams of water per gram of haloformate, preferably from about 7 grams to about 12 grams of water per gram of haloformate. A majority of the water is added as a result of adding the ingredients as a water solution.

At least one alkali metal peroxide is used in the synthesis of the peroxydicarbonates of this invention. The preferred alkali metal peroxide is sodium peroxide. The alkali peroxide is formed from reacting an inorganic peroxide such as hydrogen peroxide with an alkali metal hydroxide, such as sodium hydroxide, potassium hydroxide, ammonia hydroxide, lithium hydroxide, calcium hydroxide, magnesium hydroxide and alkali metal phosphates. The preferred sodium peroxide is formed by reacting sodium hydroxide with hydrogen peroxide. Two moles of alkali metal hydroxide are used for every one mole of inorganic peroxide. An excess of either reactant can be used, but would not be preferred.

One method to produce the peroxydicarbonates of this invention, is to use two reaction vessels. The reaction vessels may be of any shape and material, but the shape and material of construction should be conducive to being cooled. Metal vessels such as stainless steel pots or pipes are satisfactory. In one vessel, the alkali metal peroxide is produced by mixing the alkali metal hydroxide with inorganic peroxide. The mixture of the alkali metal hydroxide and inorganic peroxide are thoroughly mixed by conventional mechanical agitation to form the alkali metal peroxide. In making the preferred alkali metal peroxide, sodium hydroxide is mixed with hydrogen peroxide to produce sodium peroxide. The preferred sodium hydroxide used is a water solution of sodium hydroxide. The concentration of sodium hydroxide is not critical but the preferred concentration is a 5% to 35 weight % solution of sodium hydroxide in water, with the preferred concentration being at 5% to 15 weight % solution of sodium hydroxide. The hydrogen peroxide used is more preferably a 5% to 10 weight % solution of hydrogen peroxide in water.

The mixture used to make the alkali metal peroxide is two moles of alkali metal hydroxide with one mole of inorganic peroxide. In one embodiment, the ratio of hydroxide to peroxide ranges from about 1.8:1 to about 2.2:1. The reversible reaction can be shown for the preferred ingredients as:

$$2NaOH + H_2O_2 \Leftrightarrow Na_2O_2 + 2H_2O$$

The temperature of the reaction needs to be below the decomposition temperature of the alkali metal peroxide. Also, the mixture should be cooled so as not to add heat when later used to make the peroxydicarbonate. For the preferred alkali metal peroxide, the alkali metal peroxide is cooled to less than 28° C. and more preferably to a temperature of from 0° C. to 10° C.

In the second vessel equipped with a homogenizer apparatus and cooling means, the haloformate, dispersant and water are added. The mixture of haloformate, dispersant and water is cooled and homogenized while adding the alkali metal peroxide from the first vessel. It is preferred to start the homogenization before the alkali metal peroxide is added and continue until all of the alkali metal peroxide has been added. The temperature of the mixture of the second vessel should be maintained below the decomposition temperature of the peroxydicarbonate to be formed. For the preferred reactants, the temperature should be maintained below 40° C., preferably below 22° C. and more preferably from 0° C. to 10° C. Because water is present, the mixture should not be cooled low enough to freeze the water, although the freezing temperature of the water in the mixture is lower than 0° C. because of the presence of by-products (salts). If the temperature is above the decomposition temperature of the peroxydicarbonate formed, efficiency is lowered as the peroxydicarbonate will decompose. Decomposition can be observed by foaming caused by the liberation of oxygen or carbon dioxide when the peroxydicarbonate decomposes.

The alkali metal peroxide can be added to the second vessel at a rate which is determined by the ability to cool the second vessel, such as not to exceed the decomposition temperature of the peroxydicarbonate formed. The reaction of the alkali metal peroxide and haloformate is almost instantaneous, but is extremely exothermic. Because of the highly exothermic reaction, it is preferred to meter the alkali metal peroxide from the first vessel to the second vessel containing the haloformate over a period of from about 2 to about 20 minutes. The rate of addition of the alkali metal peroxide is dependent only on the ability to cool the reaction, such as to maintain the reaction temperature below the decomposition temperature of the peroxydicarbonate being formed.

The haloformate, dispersant and water mixture of the second vessel could be added to the first vessel containing the alkali metal peroxide but this method is less efficient in that yields of peroxydicarbonate are lower.

The levels of reactants used in the second vessel are one mole of alkali metal peroxide for every two moles of haloformate. In one embodiment, the ratio of peroxide to haloformate ranges from about 1:2 to 1:1.8. The reaction can be shown for the preferred reactants as:

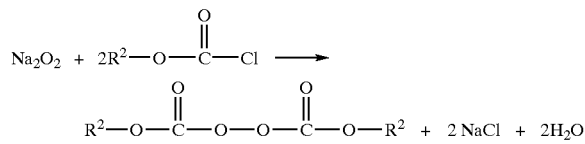

wherein $R^2$ is an ethyl group in the most preferred embodiment of this invention.

Homogenization of the ingredients in the second vessel is very important and a critical feature of this embodiment of the invention as it provides intimate contact between the reactants thus resulting in the need to use less reactants. By using less reactants, the need to dilute the reaction with a solvent or a plasticizer is unnecessary thus resulting in less by-products which are harmful in the polymerization process of the ethylenically unsaturated monomer. The homogenization also gives peroxydicarbonate droplets having a diameter less than 10 microns, preferably less than 5 microns and more preferably from 1 to 4 microns. The small droplet size of peroxydicarbonate is advantageous in producing polymers having low levels of gels.

The type of homogenizer apparatus found to be suitable for larger scale reactions in this invention is an Arde Barinco homogenizer. This type of homogenizer apparatus has a shaft extending into the reactants of the second vessel. The shaft end has narrow slits (teeth) in the fixed stator with a rotating disc having teeth offset from the teeth in the stator, such that the reactants are drawn into and repeatedly cycled through the narrow slits in the stator. For small scale laboratory reactions, a homogenizer of the tissue tearer type such as Fisher Scientific #15-338-51 can be employed.

An alternate method to make the peroxydicarbonates of this invention for use in a polymerization process to produce polymers from ethylenically unsaturated monomers, is to use an in line homogenizer. When using an in-line homogenizer, the haloformate, dispersant and water are injected into a line, such as a pipe. The pipe is connected to a homogenizer. The alkali metal peroxide may be metered into the line just prior to the homogenizer, or preferably after the homogenizer. This method provides for the homogenization of the haloformate before adding the alkali metal peroxide and homogenization after combining all ingredients. Examples of suitable in-line homogenizers are those sold by Manton Gaulin. The ingredients to be homogenized can be passed through the homogenizer multiple times until the desired homogenization is obtained, but are preferably homogenized to the desired stable emulsion droplet size in a single pass. For making the peroxydicarbonates of this invention, sufficient homogenization should be performed to give a droplet size of the peroxydicarbonate of from about 1 to 10 microns, preferably from about 1 to about 4 microns.

In one embodiment, the emulsion of haloformate is reacted to form peroxydicarbonate by continuously blending alkali metal peroxide solution into the haloformate emulsion stream with mild mixing in cooled piping or plug flow heat exchanger using the natural turbulent flow in these components. Optionally, the peroxydicarbonate may be formed by adding the hydrogen peroxide and alkali metal hydroxide solutions separately to the haloformate emulsion. In this case, it is advantageous to add the alkali metal hydroxide last to avoid undesirable hydrolysis of the haloformate. All streams are metered together in the selected ratio and pass in plug flow through a cooler and piping train to remove heat of reaction and provide sufficient residence time for the peroxydicarbonate synthesis reaction to go to completion, typically less than 30 minutes.

The line where the peroxydicarbonates are formed may be connected directly to the polymerization reactor and pumped into the reactor at the desired time.

Optionally, the line may feed a storage vessel where the peroxydicarbonate may be stored below 5° C. refrigeration, until needed for polymerization.

If it is desired to produce more than one peroxydicarbonate for use in a polymerization, then the reaction to form the first peroxydicarbonate should be completed before adding the second haloformate and the corresponding alkali metal peroxide. If two different haloformates are mixed and alkali metal peroxide is added, then three different types of peroxydicarbonates will be formed. Two types will be symmetrical with the same end groups on each end, while the third type will have a different end group on each side. Although this type of peroxydicarbonate mixture would function as an initiator for polymerization, it is not the most desirable mixture. The specific amounts of each of the three different types of peroxydicarbonates formed is not believed to be well controlled and can vary from batch to batch. For this reason, it is preferred to complete the reaction of the first peroxydicarbonate before beginning the reaction to form the second peroxydicarbonate. Should a third or subsequent peroxydicarbonate be desired, then the reaction to complete the second peroxydicarbonate should be completed before adding the haloformate to produce the third peroxydicarbonate and so forth for each additional desired peroxydicarbonate.

The reaction in the second vessel to produce the peroxydicarbonate preferably should be completed just prior to when it is needed in the polymerization cycle. Should there be an unplanned delay in using the peroxydicarbonate, the aqueous mixture in the second vessel containing the peroxydicarbonate should be agitated. It is preferred that the second vessel contain an agitation system, as well as the homogenization system. The agitation is necessary because the preferred peroxydicarbonate is heavier than the aqueous salt mixture it is suspended in and will settle to the bottom over time if not agitated. The stability of the other peroxydicarbonates, other than di-ethyl peroxydicarbonate, are greater in that they are less dense, but agitation is still preferred should the use of the peroxydicarbonate be delayed. A simple agitation is preferred rather than continuing to run the homogenizer, since the homogenizer will add heat to the aqueous dispersion of the peroxydicarbonate, which is undesirable. Any type of system for the agitation is acceptable, such as a shaft with blades or a method to bubble inert gas into the vessel, as long as the peroxydicarbonate is not allowed to settle on the bottom of the vessel.

Various peroxydicarbonates can be made by the process of this invention. The nature, or structure of the initiator produced will depend upon the particular haloformate employed in the reaction.

Peroxyesters

The processes for producing the peroxyesters described herein involve forming a mixture of at least one inorganic base and an aqueous emulsion of at least one organic hydroperoxide and at least one acylating agent comprised of droplets of the at the least one organic hydroperoxide and the at least one acylating agent having diameters of less than 10 µm. The mixture of the at least one inorganic base and the aqueous emulsion is reacted to form an aqueous emulsion of the desired peroxyester.

Organic peroxyesters have the following general formula:

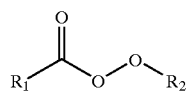
(1)

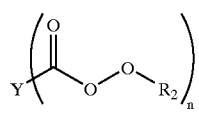
(2)

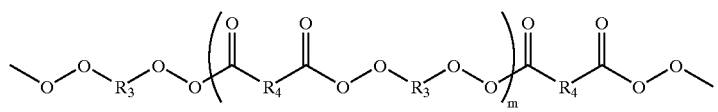
(3)

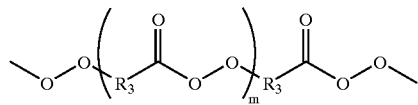
(4)

R1 and R2 are different or identical organic radicals having from 1 to 16 carbon atoms. They can be alkyl, cycloalkyl, arylalkyl, aryl, alkylaryl, or alkenyl radicals. In addition, R1 can also be a hydrogen or an alkoxy functional group. In the case of alkyl, cycloalkyl, arylalky, and alkenyl radicals, these radicals may also contain functional groups such as hydroxyl group and (or) be inserted with heteroatoms such as oxygen and sulfur in their backbones. In the case of aryl radicals, the heteroatom-containing aryl radicals are also included. While X is any organic moiety capable of bearing n —OOH groups, Y is any organic moiety capable of bearing n acyl functional groups. The n is from 2 to 6, preferably from 2 to 3. Compounds in structure (2) are usually alkylene bis(esters) of peroxycarboxylic acids such as 1,3-di (2-neodecanoylperoxy isopropyl)benzene and 2,5-dimethyl-2,5-bis(2-ethylhexanoylperoxy)hexane. Compounds in structure (3) are typically dialkyl esters of diperoxydicarboxylic acids such as di-t-butyldiperoxyazelate and di-t-butyldiperoxyphthalate. R3 and R4 are independently selected from alkylene, arylalkylene, arylene, and alkylarylene groups having 1 to 16 carbon atoms. The m is from 1 to 30, where 1 to 5 is preferred. Materials in structure (4) are typically polymers made from condensation of dihydroperoxides with diacyl chlorides. Materials in structure (5) are usually the self-condensation product of compounds containing both hydroperoxy and acyl functional groups.

Among the five formulas, the simple peroxyester (1) is the most preferred compound as its raw materials are easily accessible. Exemplary peroxyesters for structure (I) include α-cumyl peroxyneodecanoate, t-butyl peroxyneodecanoate, t-amyl peroxypivalate, t-butyl peroxypivalate, t-amyl peroxy-2-ethylhexanoate, t-butyl peroxy-2-ethylhexanoate, t-butyl peroxyisobutyrate, and t-butyl peroxy-3,3,5-trimethylhexanoate.

The following equation depicts the formation of exemplary peroxyester structures:

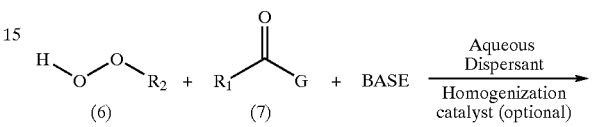

(1)

(2)

(3)

-continued

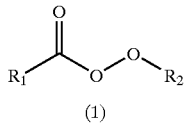
(1)

Structure (6) and (7), respectively, are the general formula for the hydroperoxides and acylating agents used to produce the peroxyesters, where R1 and R2 are the same as these described for structure (1). G in structure (7) may be a halogen atom, such as chlorine, fluorine, iodine or bromine, or a carboxylic group containing a R1 radical, or an imidazyl functional group. The structure of the imidazyl group is depicted by structure (8). In one embodiment, chlorine is the G radical. In other words, suitable (7) structures include carboxylic acid halides, acid anhydrides, 1-alkanoylimidazoles, and 1-(aryl)carbonylimidazoles. In one embodiment, the (7) structure is a carboxylic acid chloride, including neo-decanoyl chloride, pivaloyl chloride, 2-ethylhexanoyl chloride, iso-butyryl chloride, and 3,3,5-trimethylhexanoyl chloride. In one embodiment, the (6) structure includes cumene hydroperoxide, t-butyl hydroperoxide, and t-amyl hydroperoxide.

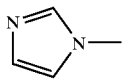

(8)

Either organic bases such as amines and pyridines or inorganic bases such as alkali metal hydroxide and carbonates can be used to promote formation of organic peroxyesters from the corresponding hydroperoxides and acylating agents. In one embodiment, inorganic bases such as NaOH and KOH are used. In one embodiment, KOH is used since it has higher alkalinity and better solubility in water at low temperature. These features are very beneficial for the quick synthesis of organic peroxyesters at low temperature.

The molar ratio among the three principal reactants, namely the organic hydroperoxide, the acylating agent, and the base can vary from 1:0.8:0.8 to 1:2:5. The ratio is generally kept at 1:1:1 when the concentration of the base is high in the reaction medium. However, excesses of the acylating agent and the base are normally needed if the peroxyester is to be produced in good yield in a dilute solution. The excess of base, if necessary, can be neutralized with an appropriate amount of diluted hydrochloric acid, sulfuric acid, or carboxylic acid. Suitable carboxylic acids include formic acid, acetic acid and stearic acid. In one embodiment, the acid for the neutralization should be the carboxylic acid from which the acylating agent is derived. The excess of base can also be consumed by synthesis of peroxydicarbonates in the formed peroxyester solution, producing a mixture of peroxyester and peroxydicarbonate in one-pot fashion. Such a mixture is often used for PVC production. The required alkalinity of the reaction media for the synthesis of peroxydicarbonates and dialkyl and diacyl peroxides is much lower that that used for peroxyester preparation. Another way to avoid using excess of reactants is to prepare the peroxyester in high concentration followed by immediate dilution in the reaction vessel with additional emulsifying agents and/or water.

Various phase transfer catalysts, such as organic quaternary ammonium salts, organic guanidinium salts, organic phosphonium salts, crown ethers, and various polyethers can be used to speed up the reaction and to reduce the usage of alkali base in the case of making diluted peroxyesters. The preferred phase transfer catalysts are polyethers such as polypropylene oxides.

At least one dispersant is used in the embodiments for the synthesis of the peroxyesters in accordance with the present invention. Exemplary dispersants are hydrolyzed polyvinyl acetates, alkyl and hydroxyalkyl cellulose ethers such as methyl cellulose or hydroxypropyl methyl cellulose, gelatin, polyvinylpyrrolidone, polyoxyethlyene sorbitan monolaurate, polyacrylic acid and like compounds. In one embodiment, the dispersant is selected to be similar to the dispersant used in the polymerization of the ethylenically unsaturated monomer. Cellulose ethers are selected for use in one embodiment. The dispersant may be added as a water solution. The level of dispersant used should be sufficient to form a water emulsion of the reactants during the peroxyester formation reaction. Typically, this level is from about 0.05 to about 0.3 gram of dispersant per gram of acylating agent, and in another embodiment, from about 0.075 to about 0.2 gram of dispersant per gram of acylating agent. When adding the dispersant as a water solution, in one embodiment, the solution has from about 1% to about 10% by weight of dispersant in water, and in another from about 2% to about 8% by weight of dispersant in water.

Water is also used in the synthesis of the peroxyesters of this invention. The water is required to dissolve the dispersant and dilute other reaction ingredients. Water also assists in the removal of the heat resulting from the exothermic reaction. Preferably the water used is demineralized water. The amount of water used in the reaction is important since it affects the alkalinity of reaction medium when a specific amount of alkali metal hydroxide is used for the synthesis of peroxyesters. Preferably a minimum amount of water is used to dissolve the dispersant, to dissolve the alkali metal hydroxide, and to achieve the required cooling. An excess of water, over that required to dilute the reactants and provide cooling, should be avoided during the reaction so as to give more intimate contact of the reactants and to provide the reaction with a strongly alkalinity medium. Once the reaction is complete, additional water may be added. Normally the amount of water used for the reaction varies from about 0.5 grams to about 20 grams of water per gram of acylating reagents, preferably from about 3 grams to about 12 grams of water per gram of the acylating agent. A majority of the water is added as a result of adding the ingredients as a water solution.

The reactants for the production of peroxyesters are subjected to conditions of agitation. Sufficient agitation should be performed to form an emulsion of the reactants with droplet sizes from about 1 to about 10 microns in one embodiment, and from about 1 to about 4 microns in another embodiment. In one embodiment, a reaction vessel equipped with a homogenizer and cooling means is used. The reaction vessel may be of any shape and material, but the shape and material of construction should be conducive to being cooled. Metal vessels such as stainless steel pots or pipes are satisfactory. To the vessel are added the organic hydroperoxide, base [in one embodiment aqueous alkali metal hydroxide], dispersant and water. The mixture is cooled and homogenized while adding the acylating agent. In one embodiment, the homogenization is started before the addition of acylating agent and continues until the entire acylating agent has been added. The temperature of the mixture of the vessel should be maintained below the decomposition temperature of the peroxyester to be formed. In one embodiment, the temperature should be maintained below about 40° C., in another embodiment below about 27° C. and in still another embodiment, from about 15° C. to about 21° C. Because water is present, the mixture should not be cooled low enough to freeze the water. An additional reason to avoid cooling the reaction mixture to a lower temperature is the potential NaOH precipitation when this base is used, although KOH does not present such a problem at these temperatures. If the temperature is above the decomposition temperature of the peroxyester, efficiency of the reaction mixture is lowered as the initiator for the intended polymerization will decompose. The reaction of the acylating agent and hydroperoxide is almost instantaneous and extremely exothermic. Because of the highly exothermic reaction, in one embodiment, the acylating agent is metered over a period of from about 1 to about 20 minutes. The rate of addition of the acylating agent depends only on the ability to cool the reaction, such as to maintain the reaction temperature below the decomposition temperature of the peroxyester being formed.

The reaction may be carried out by forming an emulsion by homogenization of the acylating agent and the hydroperoxide in water and the dispersant followed by addition of base. However, this method is less efficient, with lower peroxyester yields, which is especially true when R1 is H or has less than 4 carbon atoms.

Homogenization of the ingredients in the vessel provides intimate contact between the reactants thus resulting in the need to use less reactants. By using less reactants, the need to dilute the reaction with a solvent or a plasticizer is unnecessary thus resulting in less by-products that may be harmful in the polymerization process of the ethylenically unsaturated monomer. In one embodiment, the homogenization yields peroxyester droplets having a diameter less than about 10 microns, and less than about 5 microns in another embodiment, and from about 1 to about 4 microns in still another embodiment. The small droplet size of peroxyester in the emulsion is advantageous for producing polymers having low gel levels.

An exemplary homogenizer apparatus suitable for larger scale reactions in this invention is an Arde Barinco homogenizer. This type of homogenizer apparatus has a shaft extending into the reactants of the vessel. The shaft end has narrow slits (teeth) in the fixed stator with a rotating disc having teeth offset from the teeth in the stator, such that the reactants are drawn into and repeatedly cycled through the narrow slits in the stator. For small scale laboratory reactions, a tissue tearer homogenizer such as ESGE Model M133/1281-0 may be employed.

An alternate method to make the peroxyesters of this invention for use in a polymerization process to produce polymers from ethylenically unsaturated monomers, is to use an in-line homogenizer. When using an in-line homogenizer, the organic hydroperoxide, base, dispersant and water are injected into a line, such as a pipe. The pipe is connected to a homogenizer. The acylating agent may be metered into the line just prior to the homogenizer, or preferably in a recirculating line between homogenization passes. This method provides for the homogenization of the organic hydroperoxide before adding the acylating agent and homogenization after combining all ingredients. Suitable in-line homogenizers are those sold by Manton Gaulin, by IKA under the DISPAX line of products and Arde-Barinco under the CAVITRON product line. The ingredients to be homogenized can be passed through the homogenizer multiple times until the desired homogenization is obtained. In producing peroxyesters, sufficient homogenization should be performed to yield a peroxyester droplet size from about 1 to about 10 microns in one embodiment, and from about 1 to about 4 microns in another embodiment. The line where the peroxyesters are formed may be connected to the polymerization reactor and pumped into the reactor at the desired time. The line is flushed clean with water after the peroxyester is charged to the polymerization reactor.

If it is desired to produce more than one organic peroxide in addition to the peroxyester, then the reaction to form the peroxyester should be completed before adding the ingredients for making the second organic peroxides. In the case of the second peroxide being a diakyl, diacyl or peroxydicarbonate, excess of base is preferably used for the first reaction, the preparation of the peroxyester. The excess of base speeds up formation of the peroxyester, and the unused base is then utilized for the second reaction, the preparation of the diakyl, diacyl, or peroxydicarbonate. Should a third or subsequent organic peroxide be desired, the reaction to complete the second organic peroxide should be completed before adding the components to produce the third organic peroxide, and so forth. If two different peroxyesters sharing common R1 or R2 are needed for polymerization, they may be produced simultaneously by mixing two hydroperoxides with a common acylating agent or two acylating agents with a common hydroperoxide. Attempts to simultaneously produce two peroxyesters, without a common component, should be avoided since mixing two acylating agents and two hydroperoxides will lead to formation of four different types of peroxyesters. Although this type of peroxyester mixture would function as an initiator for polymerization, it is not the most desirable mixture. The specific amounts of each of the four different types of peroxyesters formed are difficult to control and can vary from batch to batch. For this reason, it is preferred to complete the reaction of the first peroxyester before beginning the reaction to form the second one and each additional desired organic peroxide.

Various peroxyesters can be made by the process of this invention. The nature, or structure of the initiator produced will depend upon the particular acylating agent and organic hydroperoxide employed in the reaction.

Organic Peroxide Initiators

The organic peroxides described herein are useful as initiators in the polymerization of ethylenically unsaturated monomers. Exemplary ethylenically unsaturated monomers include vinyl halides, such as vinyl chloride, vinyl bromide, etc., vinylidene halides, such as vinylidene chloride, and the like, acrylic acid; esters of acrylic acid, such as methyl acrylate, ethyl acrylate, butyl acrylate, octyl acrylate, cyanoethyl acrylate, and the like; methacrylic acid; esters of methacrylic acid such as methyl methacylate, butyl methacrylate, and the like; vinyl acetate; acrylonitrile; syrene and styrene derivatives including alpha-methyl styrene, vinyl toluene, chlorostyrene, vinyl naphthalene; and other monomers having at least one terminal $CH_2=C<$ grouping; mixtures of any one of these types of monomers and other types of ethylenically unsaturated monomers known to those skilled in the art.

A demonstration of the efficacy of the organic peroxides described herein is in the suspension polymerization of vinyl chloride to make polyvinyl chloride (PVC). In the aqueous suspension process to produce PVC from vinyl chloride monomer, the polymerization process is usually conducted at a temperature in the range of about 0° C. to about 100° C. In one embodiment, the temperature ranges from about 40° C. to about 70° C. In this temperature range, polymers having many beneficial properties are produced. The time of the polymerization reaction will vary from about 2 to about 15 hours, preferably from 3 to 6 hours. The aqueous suspension process to produce PVC contains, in addition to the vinyl chloride monomer, water, dispersants, free radical initiator and may optionally contain other ingredients such as buffers, short stop agents, and the like. The aqueous suspension process to produce PVC is a batch process for the reaction and then becomes a continuous process after leaving the reactor. The continuous part of the process involves stripping the residual vinyl chloride monomer from the PVC polymer and recovering the monomer for further use in subsequent polymerizations. Also, the polymer particles are dewatered and dried to a free flowing powder, all as is well understood in the art. Once the PVC polymerization reaction reaches the desired conversion, which is usually from about 80 to 94 percent conversion of the monomer to polymer, the reaction is stopped and the reactor contents are pumped out to empty the reactor. The empty reactor is then prepared for the next polymerization cycle by flushing with water and coating the walls to prevent build-up of polymer. The flushing and coating cycle consumes about 10 to 20 minutes, which is ample time to conduct the reaction to make the organic peroxide that will be used in the next polymerization cycle.

The organic peroxides of the present invention, together with any by-products of the organic peroxide production reaction are charged to the PVC reactor at the desired time to begin the polymerization of the vinyl chloride monomer. The order of charging the ingredients to the PVC reactor is not critical, however it is preferred to charge the organic peroxide after the reactor contents have reached the desired polymerization temperature. If the organic peroxide is added before the desired polymerization temperature is reached, some of it will be consumed at the lower temperature, resulting in less initiator being present for the polymerization. This can be compensated for by adding an excess of organic peroxide, but is less desirable because of increased costs.

The yields of the organic peroxide preparation method are typically from about 90 to about 97% yield. A convenient method to determine the yield is to measure the PVC reaction cycle time with a given loading of organic peroxide and compare the reaction time to the theoretical time. This method is well understood in the art. The PVC reaction cycle times indicate that the yields of the organic peroxides are very reproducible and are typically at least 90%. A convenient polymerization method is to the charge to the polymerication reactor about 10% excess over the theoretical amount required of the organic peroxide produced by this invention. This is to compensate for the less than 100% organic peroxide yield.

The level and selection of a particular type of organic peroxide used in a PVC polymerization reaction will vary depending on the reaction temperature desired and the total reaction cycle time desired. The total cycle time desired is usually determined by the speed at which heat can be removed from the PVC reaction. The speed of heat removal depends on several factors such as the surface area of the reactor available for cooling, the cooling medium temperature, and the coefficient of heat transfer. PVC reactors can be equipped with reflux condensers to enhance the speed of cooling and refrigerated water can be used on the reactor jacket as well as internal cooling surfaces such as baffles.

In one embodiment, levels of organic peroxides used are from about 0.20 to about 1 part by weight per 100 parts by weight of vinyl chloride monomer, in another embodiment from about 0.030 to about 0.060 part by weight per 100 parts by weight of vinyl chloride monomer. Different organic peroxides require different levels, depending on their decomposition rate to form free radicals at a given reaction temperature, and their molecular weight, all is well understood by those skilled in the art. Conventional organic peroxides or other initiators may be used in conjunction with the organic peroxides produced as described herein to achieve specific desired reaction kinetics. However, this is typically unnecessary, since multiple organic peroxides can be produced by the method of this invention.

One aspect of this invention is that the entire contents of the vessel where the organic peroxide is produced may be charged to the PVC polymerization reactor. There is no need to purify the organic peroxide nor to dilute it with solvents or plasticizers as is taught by the prior art methods.

The organic peroxides are preferably made on demand, one batch at a time, as needed. This eliminates the need to store the organic peroxide. Of course, the organic peroxides could be made by the method of this invention and stored for later use, but this is less desirable.

EXAMPLES

The following Examples are presented to show the method of making peroxydicarbonate organic peroxides and their subsequent use to produce PVC polymers.

Example 1

In this Example di-ethyl peroxydicarbonate is produced. The preparation of the peroxydicarbonate is carried out in a fume hood. An Arde Barinko homogenizer unit is used. A 15 liter beaker is placed within an acetone-dry ice cooling bath held at approximately −10° C. In addition, an ethylene glycol cooling coil is placed within the beaker. Temperatures of both the reaction mixture and the external cooling bath are monitored continuously via glass thermometers clamped in place. The cooling coil operates at from 4° C. to 10° C. 1200 milliliters of water was placed within the 15 liter steel beaker, followed by 1,000 milliliters of 5 weight percent in water of 72.5% hydrolyzed poly vinyl acetate dispersant and 541 milliliters (596 grams) of ethyl chloroformate. This mixture was homogenized with an Arde Barinko homogenizer for approximately one minute, to facilitate the formation of an emulsion of ethyl chloroformate.

In a separate glass beaker, placed within an ice bath, 4154 milliliters (4391 grams) of a 5 weight percent in water of sodium hydroxide was mixed with 280 milliliters (311 grams) of a 30 weight percent in water of hydrogen peroxide. Mechanical agitation was used in the glass beaker. The mixture was stirred mechanically for approximately 5 minutes, to facilitate the formation of sodium peroxide (which is formed in equilibrium with sodium hydroxide and hydrogen peroxide) as represented by the formula:

$$2NaOH + H_2O_2 \leftrightarrow Na_2O_2 + 2H_2O$$

This mixture containing the sodium peroxide was then placed within a glass dropping funnel which was securely clamped above the 15 liter stainless steel beaker containing the ethyl chloroformate. The temperature within the steel beaker was 0° C. The homogenizer was running throughout the synthesis reaction to form the peroxydicarbonate.

The sodium peroxide was added dropwise from the glass dropping funnel, with the addition rate manually adjusted such that the temperature of the reaction mixture did not rise above 10° C. The reaction of the sodium peroxide with the ethyl chloroformate can be represented by the formula:

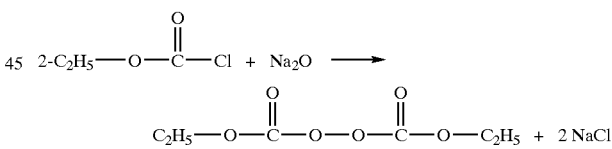

At the end of the addition of the sodium peroxide, which was from 10–15 minutes, the reaction mixture was homogenized for a further 5 minutes while an additional 3500 milliliters of a 5 weight percent in water of 72.5% hydrolyzed poly vinyl acetate was added to stabilize the di-ethyl peroxydicarbonate emulsion.

On a 100% yield basis there would be 489 grams of di-ethyl peroxydicarbonate produced.

The mixture now contains all of the di-ethyl peroxydicarbonate and 72.5% hydrolyzed poly vinyl acetate necessary to provide a dispersed initiator charge for a 4.2 cubic meter size reactor to polymerize vinyl chloride.

If one wishes to produce different peroxydicarbonates, other than di-ethyl peroxydicarbonate, to achieve the same activity on an active oxygen basis, different amounts of the chloroformate would be required in the procedure described above according to the following table:

TABLE I

| Peroxydicarbonate made | Chloroformate used | Amount chloroformate used | |
|---|---|---|---|
| | | Grams | Milliliters |
| Di-ethyl peroxydicarbonate | Ethyl chloroformate | 596 | 541 |
| n-propyl peroxydicarbonate | n-propyl chloroformate | 673 | 617 |
| Iso-propyl peroxydicarbonate | Iso-propyl chloroformate | 673 | 624 |
| n-butyl peroxydicarbonate | n-butyl chloroformate | 750 | 698 |
| s-butyl peroxydicarbonate | s-butyl chloroformate | 750 | 714 |
| 2-ethyl hexyl peroxydicarbonate | 2-ethyl hexyl chloroformate | 1058 | 1080 |

The amounts of the other ingredients (other than the chloroformate) and the procedure would be the same as described above for making di-ethyl chloroformate.

Example 2

This example is presented to show a vinyl chloride suspension polymerization using the di-ethyl peroxydicarbonate produced in Example 1.

To a clean 4.2 cubic meter polymerization reactor equipped with agitation and cooling was added 1,479.86 kg of vinyl chloride monomer, 2,013.278 kg of hot demineralized water, 3.9173 kg of methyl cellulose dispersant, 2.5243 kg of 88% hydrolyzed poly vinyl acetate dispersant and the aqueous di-ethyl peroxydicarbonate emulsion produced in Example 1. The reaction was started at 56.5° C. and held at this temperature for 45 minutes. At 45 minutes the reaction temperature was reduced by 0.038° C. per minute for 185 minutes to a reaction temperature of 49.5° C. The reaction temperature was held at 49.5° C. until a pressure drop occurred. At 312 minutes after the addition of the initiator a pressure drop occurred and 591.9 grams of a short-stop agent were added to terminate the reaction. The PVC slurry was stripped of residual monomer and dried. Examination of the internal metal surfaces of the polymerization vessel showed that the vessel was unexpectedly lacking in polymer build-up, which is very advantageous.

This example demonstrates that the di-ethyl peroxydicarbonate produced in Example 1 was very effective in polymerizing vinyl chloride monomer.

Example 3

This example is presented to show a standard control vinyl chloride suspension polymerization using a commercially available sec-butyl peroxydicarbonate. The same polymerization vessel (4.2 cubic meters), and reaction ingredients and procedures were followed as in Example 2, except that 669 grams of sec-butyl peroxydicarbonate was used as the initiator. At 291 minutes after the addition of the initiator, a pressure drop occurred and the short-stop agent was added. The PVC slurry was stripped of residual monomer and dried. An examination of the internal surfaces indicated that there was some polymer build-up, which is normal for this type of reaction. The polymer build up was greater for this reaction than for the reaction of Example 2, which uses the peroxydicarbonate produced by this invention.

Example 4

This example when compared with Example 5 and 6 is presented to show the superiority of using the di-ethyl peroxydicarbonate produced by this invention over that used in the prior art method of producing the peroxydicarbonate in the PVC reactor vessel. This example is a control for Examples 5 and 6.

A vinyl chloride suspension reaction was conducted in a 55 liter polymerization vessel equipped with agitation and cooling. To a clean 55 liter reactor vessel, the following polymerization ingredients were added:

| | |
|---|---|
| demineralized water | −25.440 Kg |
| Vinyl chloride monomer | −18.544 Kg |
| PVA (72.5%) | −439.898 gr |
| Methyl cellulose | −68.681 gr |
| PVA (88%) | −35.210 gr |
| Sec-butyl peroxydicarbonate | −8.396 gr |

The water was first added and the agitator started. The VCM was added and the reactor contents were heated to 56° C. The dispersants were then added and agitation continued while maintaining the temperature at 56° C. for 10 minutes. At this time the commercially available initiator, secondary-butyl peroxydicarbonate, was added and the reaction started. The reaction temperature was maintained at 56° C. for 49 minutes. The reaction temperature was gradually reduced as in Example 2 for 197 minutes until it reached 50° C. The temperature was maintained at 50° C. until pressure drop occurred. Pressure drop occurred at 272 minutes after adding the initiator, at which time the reaction was terminated by adding 3.709 gr of a short-stop agent. The PVC resin slurry was stripped of residual monomer and dried.

Example 5

This example is presented to show that a vinyl chloride suspension reaction using the di-ethyl peroxydicarbonate produced by the method of this invention is superior to the method used in the prior art of producing the di-ethyl peroxydicarbonate in the polymerization vessel (as is shown in Example 6).

The same 55 liter reactor vessel was used in this example as in Example 4 and the same procedures followed as well as the same reaction ingredients, except that the 8.396 grams of commercially available secondary butyl peroxydicarbonate was replaced with a di-ethyl peroxydicarbonate produced as in Example 1 using 8.56 grams of ethyl chloroformate. Pressure drop occurred at 274 minutes after addition of the initiator and the reaction was terminated at this time by adding a short stop agent as in Example 4. The PVC resin slurry was stripped of residual monomer and dried.

Example 6

This example is presented to show the suspension polymerization of vinyl chloride monomer using the prior art method of making di-ethyl peroxydicarbonate in the polymerization vessel, prior to the polymerization.

The same 55 liter reactor was used in this example as in Examples 4 and 5 and the sane procedures followed as well as the same reaction ingredients, except that in this example the di-ethyl peroxydicarbonate was produced in the reaction vessel and about a 35% excess of initiator ingredients were used to obtain an equivalent time to pressure drop, because of the inefficiency in making the peroxydicarbonate in the reactor vessel.

To make the initiator in the reactor, 8.1 Kg of water was first charged to the reactor (which is about 32% of the total water used) and the agitator started. It was necessary to have the water level higher than the agitator level in the reactor in order to get agitation for making the initiator. The dispersants (72.5% PVA, 88% PVC and methyl cellulose) were then charged to the reactor and followed by 10.50 grams of ethyl chloroformate, 15.4276 grams of sodium hydroxide, and 5.5628 grams of hydrogen peroxide. The ingredients were mixed for 5 minutes before charging the remaining water. The vinyl chloride monomer was then charged and temperature brought to 56° C. The temperature profile was then the same as in Examples 4 and 5. Pressure drop occurred at 277 minutes and the reaction was stopped as in Examples 4 and 5. The resulting PVC resin slurry was dewatered and dried.

The PVC resins produced in Examples 4, 5 and 6 were tested for properties important to PVC resins and the results are shown in Table II below:

TABLE II

| Resin Property | Example 4 (control) | Example 5 (this invention) | Example 6 (comparative) |
| --- | --- | --- | --- |
| Avg particle size (microns) | 126 | 131 | 146 |
| Particle size distribution | 23 | 23 | 27 |
| % coarse | 0.10 | 0 | 0.10 |
| % fines | 21.48 | 19.40 | 12.61 |
| DOP porosity (ml/gr.) | 0.414 | 0.394 | 0.361 |
| Apparent bulk density (gr/ml.) | 0.419 | 0.424 | 0.452 |
| Funnel flow (seconds) | 28.4 | 27.0 | 22 |
| Yellowness Index | 8.07 | 11.63 | 14.54 |
| DTS-yellow (min) | 14 | 18 | 10 |
| DTS-black (min) | 24 | 29 | 22 |

From the above data it can be seen that the thermal stability and initial color (yellowness index) of the PVC resin made with the initiator produced in the reaction vessel (Example 6) is inferior to the PVC resin produced according to this invention (Example 5). The resin produced by this invention compares much more favorably to the control (Example 4) which uses a conventional commercially available sec-butyl peroxydicarbonate initiator. The yellowness index and the stability (DTS) problems of the prior art method are believed to be caused by the low yield of peroxydicarbonates made in the reactor thus resulting in significant amounts of chloroformate not being converted to peroxydicarbonate due to hydrolysis to ethyl carbonic acid and the resulting detrimental effects on the PVC resin by having these contaminants present in the polymerization.

Example 7

In this Example di-2-ethylhexyl peroxydicarbonate was produced in a continuous process. The bench scale apparatus for the preparation of the peroxydicarbonate was contained within a fume hood. An ESGE™ homogenizer Model M 133/1281-0 unit with large mixing head was positioned near the bottom of a 600 milliliter glass beaker. 188.57 grams of a 2.5 weight percent in water solution of hydroxypropyl methyl cellulose dispersant was placed in the 600 milliliter glass beaker followed by 111.57 grams of di-2-ethylhexyl chloroformate. This mixture was homogenized at room temperature (19 to 23° C.) with the ESGE™ homogenizer for approximately five minutes, to facilitate the formation of a stable emulsion of di-2-ethylhexyl chloroformate with droplet size ranging from less than 1 micron to 10 microns in diameter.

In a separate 400 milliliter glass beaker, 335.12 grams of a 7.03 weight percent in water solution of sodium hydroxide was prepared at room temperature. A separate 50 milliliter glass beaker was used to prepare 28.124 grams of a 35.6 weight percent in water solution of hydrogen peroxide at room temperature.

Three Cole-Parmer MasterFlex L/S™ Digital Standard Drives with standard peristaltic pump heads were connected with tubing to deliver the three raw materials in controlled ratio. They were adjusted to deliver 4.23 grams per minute of stable chloroformate emulsion, 4.72 grams per minute of sodium hydroxide solution and 0.40 grams per minute of hydrogen peroxide solution. This ratio represented a 2 percent excess of both sodium hydroxide and hydrogen peroxide to assure complete conversion of the chloroformate to peroxydicarbonate and the absence of any residual 2-ethylhexyl chloroformate.

The three streams were combined in $1/8^{th}$ inch tubing using standard tees, first adding hydrogen peroxide solution to the stable chloroformate emulsion, then adding the sodium hydroxide solution. The final tee connected to a 20 foot length of $1/8^{th}$ inch diameter tubing coiled to an 8 inch diameter within a ten inch plastic water bath. The $1/8^{th}$ inch tubing connected to a 50 foot length of $1/4^{th}$ inch tubing coiled within the same bath. The combination of tubing coils provided approximately 30 minutes of residence time. Water temperature in the bath was held at 21 to 23 degrees Celsius. Heat of formation of the peroxydicarbonate was distributed over the first several feet of tubing in the bath and it was not difficult to keep the reaction temperature within the 21 to 27° C. range.

The tubing coil was initially full of demineralized water, so product began to emerge after 30 minutes of operation and collection was started after 40 minutes of operation. After 70 minutes all raw materials had been delivered, demineralized flush water was added to each beaker and pumping continued for another 30 minutes. Collection of product was terminated after 90 minutes of operation. Discarding the first and last ten minutes of dispersion produced in this example assured undiluted product for evaluation.

The method of this Example will produce a dispersion containing 15.074% di-2-ethylhexyl peroxydicarbonate by weight based on a 100% yield of peroxydicarbonate from haloformate. This would be 663.39 grams of dispersion containing 100 grams of di-2-ethylhexyl peroxydicarbonate if all were collected. In view of the material discarded at the beginning and end of the operation, 570 grams of dispersion was collected.

The dispersion was evaluated in several ways. First, residual chloroformate was measured to confirm high conversion. Test results indicated less than 200 ppm chloroformate remained, equivalent to 99.9% conversion. Second, the dispersion was analyzed using ASTM E298-01 Standard Test Methods for Assay of Organic Peroxides. The average of three assays of di-2-ethylhexyl peroxydicarbonate concentration was 14.85 percent indicating 98.5 percent conversion of chloroform ate to peroxydicarbonate. Third, aliquots of the dispersion were used to conduct PVC polymerizations and reaction times were compared with controls produced with commercial di-2-ethylhexyl peroxydicarbonate. Comparing 20 experimental polymerizations with 12 controls, the experimental reactions ran 1.7 percent faster than the controls with identical standard deviations in the reaction times. This evidence confirmed the concentration of active initiator in the dispersion.

The following Examples demonstrate methods of producing diacyl organic peroxides.

Example 8

In this example, diisobutyryl peroxide is produced. The preparation of the peroxide was carried out in a fume hood.

An ESGE laboratory homogenizer unit (½ inch diameter head) was used. A 250 milliliter stainless steel beaker was placed within an ice-water cooling bath held at approximately OD C. The temperature of the reaction mixture was monitored continuously via a thermocouple clamped in place. 45 milliliters of 4.66 weight percent aqueous solution of 72.5% hydrolyzed poly(vinyl acetate) was placed within the beaker, followed by 10.92 milliliters (12.09 grams) of isobutyryl chloride. This mixture was homogenized with an ESGE homogenizer for approximately two minutes, to facilitate the formation of an emulsion of isobutyryl chloride.

In a separate 100 milliliter glass beaker, placed within an ice bath, 86.46 milliliters (91.13 grams) of a 5 weight percent solution in water of sodium hydroxide was mixed with 5.78 milliliters (6.41 grams) of a 30 weight percent solution in water of hydrogen peroxide. Mechanical agitation was used in the glass beaker. The mixture was stirred mechanically for approximately 5 minutes. Sodium peroxide was formed in equilibrium with sodium hydroxide and hydrogen peroxide as represented by the formula:

$$2NaOH + H_2O_2 \Leftrightarrow Na_2O_2 + 2H_2O$$

This mixture containing the sodium peroxide was then placed within a glass dropping funnel which was securely clamped above the 250 milliliter stainless steel beaker containing the isobutyryl chloride. The temperature within the steel beaker was 0° C. The homogenizer was running throughout the synthesis reaction to form the diisobutyryl peroxide.

The sodium peroxide was added dropwise from the glass dropping funnel, with the addition rate manually adjusted such that the temperature of the reaction mixture did not rise above 10° C. The reaction of the sodium peroxide with the isobutyryl chloride can be represented by the formula:

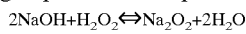

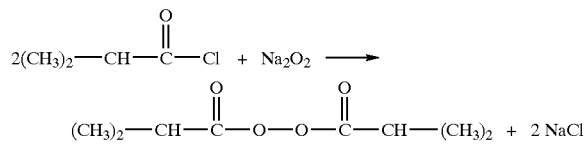

At the end of the addition of the sodium peroxide, which was from 2–5 minutes, the reaction mixture was homogenized for a further 2 minutes.

Based on $^{13}C$ nmr spectroscopic examination of the product emulsion, recorded at 75.4 MHz, the conversion of the isobutyryl chloride to diisobutyryl peroxide had proceeded to 96–98%.

The resulting mixture contained all of the diisobutyryl peroxide and 72.5% hydrolyzed poly(vinyl acetate) necessary to provide a dispersed initiator charge for a 4.2 cubic meter size reactor to polymerize vinyl chloride.

If one wishes to produce a different diacyl peroxide, other than diisobutyryl peroxide, to achieve the same activity on an active oxygen basis, different amounts of the acyl halide, on a molecular weight basis, would be required in the procedure described above.

The amounts of the other ingredients (other than the isobutyryl chloride) and the procedure can be the same as described above for making diisobutyryl peroxide.

Example 9

In this example, dibenzoyl peroxide is produced. The preparation of the peroxide was carried out in a fume hood. An ESGE laboratory homogenizer unit (½ inch diameter head) was used. A 250 milliliter stainless steel beaker was placed within an ice-water cooling bath held at approximately 0° C. The temperature of the reaction mixture was monitored continuously via a thermocouple clamped in place. 45 milliliters of 4.66 weight percent aqueous solution of 72.5% hydrolyzed poly(vinyl acetate) was placed within the beaker, followed by 13.49 milliliters (16.34 grams) of benzoyl chloride. This mixture was homogenized with an ESGE homogenizer for approximately two minutes, to facilitate the formation of an emulsion of benzoyl chloride.

In a separate 100 milliliter glass beaker, placed within an ice bath, 86.46 milliliters (91.13 grams) of a 5 weight percent solution in water of sodium hydroxide was mixed with 5.78 milliliters (6.41 grams) of a 30 weight percent solution in water of hydrogen peroxide. Mechanical agitation was used in the glass beaker. The mixture was stirred mechanically for approximately 5 minutes Sodium peroxide was formed in equilibrium with sodium hydroxide and hydrogen peroxide as represented by the formula:

$$2NaOH + H_2O_2 \Leftrightarrow Na_2O_2 + 2H_2O$$

This mixture containing the sodium peroxide was then placed within a glass dropping funnel which was securely clamped above the 250 milliliter stainless steel beaker containing the benzoyl chloride. The temperature within the steel beaker was 0° C. The homogenizer was running throughout the synthesis reaction to form the dibenzoyl peroxide.

The sodium peroxide was added dropwise from the glass dropping funnel, with the addition rate manually adjusted such that the temperature of the reaction mixture did not rise above 20° C. The reaction of the sodium peroxide with the benzoyl chloride can be represented by the formula:

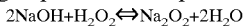

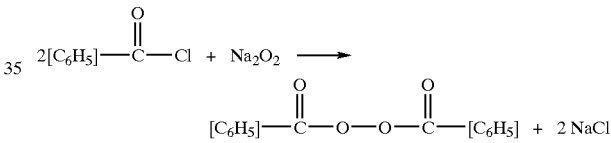

At the end of the addition of the sodium peroxide, which was from 2–5 minutes, the reaction mixture was homogenized for a further 2 minutes.

Based on $^{13}C$ nmr spectroscopic examination of the product emulsion, recorded at 75.4 MHz, the conversion of the benzoyl chloride to dibenzoyl peroxide had proceeded to 96–98%.

The resulting mixture contained all of the dibenzoyl peroxide and 72.5% hydrolyzed poly(vinyl acetate) necessary to provide a dispersed initiator charge for a 4.2 cubic meter size reactor to polymerize vinyl chloride.

If one wishes to produce a different diacyl peroxide, other than dibenzoyl peroxide, to achieve the same activity on an active oxygen basis, different amounts of the acyl halide, on a molecular weight basis, would be required in the procedure described above.

The amounts of the other ingredients (other than the benzoyl chloride) and the procedure can be the same as described above for making dibenzoyl peroxide.

The following Examples demonstrate methods of producing peroxyesters useful as initiators for polymerization reaction. All experiments illustrated here use synthesis of a-cumyl peroxyneodecanoate (CPN) starting from cumene hydroperoxide (CHP) and neo-decanoyl chloride (NDC) as examples.

Examples 10–24

Table III (Examples 10–16) illustrates the relationship between CPN yield and the molar ratio among CHP, NDC and NaOH. The dispersant used for the study was 3.5% Methocel F50 (F50) and the reaction temperatures were all controlled below 21° C. Table IV (Examples 17–24) illustrates the relationship between CPN yield and the molar ratio among CHP, NDC and KOH. The dispersant used for the study was 3.5% Methocel F50 (F50) and the reaction temperatures were all controlled below 21° C.

To a 40 ml glass vial were added 2.11 g of 80% cumene hydroperoxide and a solution of corresponding amount of base in 12.85 g of 3.5% Methocel F50 solution followed by inserting a glass jacket housing a J type thermocouple and a homogenizer into the reaction mixture. The homogenizer was then turned on with the reaction vessel cooled with cold water. After the reaction mixture reached 15° C., addition of corresponding amount NDC started. After addition of NDC was finished, the reaction was then continued for additional ten minutes. During this period of time, the reaction temperature was maintained at or below 21° C. The reaction mixture was then analyzed with HPLC to determine the CPN yield.

TABLE III

| Example | Dispersant | CHP:NDC:NaOH | Yield of CPN (%) |
|---|---|---|---|
| 10 | 3.5% F50 | 1:1.03:1.09 | 41.0 |
| 11 | 3.5% F50 | 1:1.03:2.16 | 61.4 |
| 12 | 3.5% F50 | 1:1.54:2.16 | 62.2 |
| 13 | 3.5% F50 | 1:1.54:2.60 | 70.5 |
| 14 | 3.5% F50 | 1:1.54:3.15 | 75.7 |
| 15 | 3.5% F50 | 1:1.54:3.70 | 72.5 |
| 16 | 3.5% F50 | 1:1.54:4.27 | 82.0 |

TABLE IV

| Example | Dispersant | CHP:NDC:KOH | Yield of CPN (%) |
|---|---|---|---|
| 17 | 3.5% F50 | 1:1.03:1.09 | 60.9 |
| 18 | 3.5% F50 | 1:1.03:2.16 | 69.0 |
| 19 | 3.5% F50 | 1:1.54:2.16 | 80.0 |
| 20 | 3.5% F50 | 1:1.54:2.60 | 85.8 |
| 21 | 3.5% F50 | 1:1.54:3.14 | 91.1 |
| 22 | 3,5% F50 | 1:1.54:3.70 | 94.1 |
| 23 | 3.5% F50 | 1:1.54:4.26 | 93.8 |
| 24 | 3.5% F50 | 1:1.80:4.26 | 98.5 |

As illustrated by the Examples, excess of NDC and bases are needed to achieve high conversion of CHP to CPN when CPN is to be prepared in the range of 6% to 10% by weight in the reaction mixture. It is also noticeable that stronger base KOH is much more efficient in promoting formation of CPN under the reaction conditions.

Examples 25–43

Table V (Examples 25–31) illustrates the relationship between CPN yield and the molar ratio among CHP, NDC and NaOH using 3.5% Methocel E50 (E50) as dispersant. Table VI (Examples 32–44) illustrates the relationship between CPN yield and the molar ratio among CHP, NDC and KOH using 3.5% Methocel E50 (E50) as dispersant. All reaction temperatures were all controlled below 21° C.

To a 40 ml glass vial were added 2.11 g of 80% cumene hydroperoxide and a solution of corresponding amount of base in 12.85 g of 3.5% Methocel E50 solution followed by inserting a glass jacket housing a J type thermocouple and a homogenizer into the reaction mixture. The homogenizer was and turned on with the reaction vessel cooled with cold water. After the reaction mixture reached 15° C., addition of corresponding amount NDC started. After addition of NDC was finished, the reaction was then continued for additional ten minutes. During this period of time, the reaction temperature was maintained at and below 21° C. The reaction mixture was then analyzed with HPLC to determine the CPN yield.

TABLE V

| Example | Dispersant | CHP:NDC:NaOH | Yield of CPN (%) |
|---|---|---|---|
| 25 | 3.5% E50 | 1:1.03:1.10 | 44.0 |
| 26 | 3.5% E50 | 1:1.03:2.17 | 63.9 |
| 27 | 3.5% E50 | 1:1.54:2.16 | 64.5 |
| 28 | 3.5% E50 | 1:1.54:2.60 | 70.6 |
| 29 | 3.5% E50 | 1:1.54:3.15 | 77.1 |
| 30 | 3.5% E50 | 1:1.54:3.70 | 81.3 |
| 31 | 3.5% E50 | 1:1.54:4.26 | 84.8 |

TABLE VI

| Example | Dispersant | CHP:NDC:KOH | Yield of CPN (%) |
|---|---|---|---|
| 32 | 3.5% E50 | 1:1.03:1.08 | 53.1 |
| 33 | 3.5% E50 | 1:1.03:2.16 | 67.9 |
| 34 | 3.5% E50 | 1:1.54:2.16 | 80.5 |
| 35 | 3.5% E50 | 1:2.05:2.17 | 83.3 |
| 36 | 3.5% E50 | 1:1.54:2.61 | 86.4 |
| 37 | 3.5% E50 | 1:1.54:3.15 | 90.4 |
| 38 | 3.5% E50 | 1:1.54:3.69 | 94.1 |
| 39 | 3.5% E50 | 1:1.54:4.26 | 97.3 |
| 40 | 3.5% E50 | 1:1.82:4.26 | 99.8 |
| 41 | 3.5% E50 | 1:1.54:1.08 | 45.0 |
| 42 | 3.5% E50 | 1:1.50:1.50 | 63.3 |
| 43 | 3.5% E50 | 1:2.00:1.08 | 51.8 |
| 44 | 3.5% E50 | 1:2.00:1.50 | 65.8 |

The Examples again show that excess of NDC and base are useful to achieve high conversion of CHP to CPN when CPN is prepared in the range of 6–10% by weight in the reaction mixture. The results also demonstrate that a stronger base such as KOH is much more efficient in promoting formation of CPN under the reaction conditions. In addition, Methocel E50 and F50 behave similarly as the dispersants for the reaction.

Examples 45–46

In these Examples the relationship between the reaction time and CPN yield was examined. In all cases, molar ratio were kept at 1:2:2.4 among CHP, NDC and KOH. The dispersant in the study was 3.5% Methocel F 50 (F50). The preparation of the peroxyester is carried out in a fume hood.

To a 40 ml glass vial were added 2.11 g of 80% cumene hydroperoxide and a solution of 1.76 g of 85% KOH in 12.85 g of aqueous Methocel F50 solution followed by inserting a glass jacket housing a J type thermocouple and a homogenizer into the reaction mixture. The homogenizer was then turned on with the reaction vessel cooled with cold water. After the reaction mixture reached 15° C., addition of 4.12 g of 98% NDC started. After addition of NDC was finished, the reaction was then continued for additional specific amount of time as shown in Table VII. During this period of time, the reaction temperature was maintained at or below 21° C. The reaction mixture was then analyzed with HPLC to determine the reaction yield.

TABLE VII

| Example | Time (Min.) | CHP:NDC:BASE | Yield of CPN (%) |
|---|---|---|---|
| 45 | 10 | 1:2:2.4 | 64.0 |
| 46 | 60 | 1:2:2.4 | 69.8 |

As illustrated by the Examples, the reaction is almost completed in ten minutes. Prolonged reaction time is probably unnecessary.

Examples 47–49

In these Examples the effect of base concentration on the yield of CPN was examined. In all cases, the molar ratio among CHP, NDC and KOH were kept at 1:1.05:1.11 with the amount of the dispersant, 3.5% Methocel F 50 (F50) as variable. The preparation of the peroxyester is carried out in a fume hood.

To a 40 ml glass vial were added 2.11 g of 80% cumene hydroperoxide and a solution of 0.8 µg of 85% KOH in a specific amount of aqueous Methocel E50 solution followed by inserting a glass jacket housing a J type thermocouple and a homogenizer into the reaction mixture. The homogenizer was then turned on with the reaction vessel cooled with cold water. After the reaction mixture reached 15° C., addition of 2.22 g of 98% NDC started. After addition of NDC was finished, the reaction was then continued for additional thirty minutes. During this period of time, the reaction temperature was maintained at or below 21° C. The reaction mixture was then analyzed with HPLC to determine the yield of CPN.

TABLE VIII

| Example | 2.5% E50 (g) | CHP:NDC:KOH | Yield of CPN (%) |
|---|---|---|---|
| 47 | 17.2 | 1:1.05:1.11 | 52.3 |
| 48 | 8.6 | 1:1.05:1.11 | 63.0 |
| 49 | 4.3 | 1:1.05:1.11 | 70.8 |

As illustrated by the Examples, the reaction yield increases when the amount of emulsifying agent is reduced. Once again, the results illustrated the effect of the basicity of reaction medium.

Examples 50–66

In these Examples various polyethers were examined as potential phase transfer catalysts for the synthesis of peroxyesters. In all cases, 3.5% Methocel F 50 (F50) was used as the dispersant for the reaction. The preparation of the peroxyester is carried out in a fume hood. In the case of abbreviation used in the Tables, PEG stands for poly(ethylene glycol); PPG for poly(propylene glycol); T(PG)ME for tri(propylene glycol) methyl ether; T(EG)DM for tri(ethylene glycol)dimethyl ether; and Tetra(EG)DM for tetra(ethylene glycol) dimethyl ether. The numbers affixed to the abbreviation indicate the molecular weight of the polyethers.

To a 40 ml glass vial were added 2.11 g of 80% cumene hydroperoxide, the phase transfer catalyst, and a solution of 1.90 g of 85% KOH in 12.85 g of aqueous Methocel F50 solution followed by inserting a glass jacket housing a J type thermocouple and a homogenizer into the reaction mixture. The homogenizer was then turned on with the reaction vessel cooled with cold water. After the reaction mixture reached 21° C., addition of the needed NDC started. After addition of NDC was finished, the reaction was then continued for additional ten minutes. During this period of time, the reaction temperature was maintained at or below 21° C. The reaction mixture was then analyzed with HPLC to determine the yield of CPN.

TABLE IX

| Example | Agent | CHP:NDC:KOH | Yield of CPN (%) |
|---|---|---|---|
| Control | | 1:1.54:2.60 | 84.5 |
| 50 | 1.0 g PEG 600 | 1:1.54:2.60 | 83.1 |
| 51 | 1.0 g PEG 1000 | 1:1.54:2.60 | 83.8 |
| 52 | 1.0 g PEG 1500 | 1:1.54:2.60 | 84.4 |
| 53 | 1.0 g PEG 2000 | 1:1.54:2.60 | 81.4 |
| 54 | 1.0 g PEG 3400 | 1:1.54:2.60 | 79.3 |
| 55 | 1.0 g PEG 4600 | 1:1.54:2.60 | 79.9 |

TABLE X

| Example | Agent | CHP:NDC:KOH | Yield of CPN (%) |
|---|---|---|---|
| Control | | 1:1.54:2.60 | 84.5 |
| 56 | 1.0 g PPG 425 | 1:1.54:2.60 | 91.4 |
| 57 | 2.0 g PPG 425 | 1:1.54:2.60 | 89.5 |
| 58 | 1.0 g PPG 725 | 1:1.54:2.60 | 89.3 |
| 59 | 2.0 g PPG 725 | 1:1.54:2.60 | 89.0 |
| 60 | 1.0 g PPG 1000 | 1:1.54:2.60 | 85.0 |
| 61 | 1.0 g PPG 2000 | 1:1.54:2.60 | 81.8 |
| 62 | 1.0 g PPG 2700 | 1:1.54:2.60 | 79.9 |
| 63 | 1.0 g PPG 3500 | 1:1.54:2.60 | 78.6 |

TABLE XI

| Example | Agent | CHP:NDC:KOH | Yield of CPN (%) |
|---|---|---|---|
| Control | | 1:1.54:2.16 | 78.5 |
| 64 | 2.0 g T(PG)ME | 1:1.54:2.16 | 86.1 |
| 65 | 2.0 g T(EG)DM | 1:1.54:2.16 | 82.0 |
| 66 | 2.0 g Tetra(EG)DM | 1:1.54:2.16 | 82.5 |

As illustrated by the Examples, the poly(propylene glycol) related compounds can improve the CPN yield under the reaction conditions. On the other hand, no such effect was observed with the use of poly(ethylene glycol).

Examples 67–76

In these Examples various organic ammonium and phosphonium salts were examined as potential phase transfer catalysts for the synthesis of the peroxyester. In all cases, the 2.5% Methocel E50 was used as the dispersant for the reaction. The preparation of the peroxyester is carried out in a fume hood. In the case of abbreviation used in the tables, TBAHS stands for tetrabutylammonium hydrogen sulfate; CTMAC for cetyltrimethylammonium chloride; TBAB for tetrabutylammonium bromide; TBAFTH for tetrabutylammonium floride trihydrate; TPPB for tetraphenylphosphonium bromide for tetrabutylphosphonium bromide; and TPPC for tetraphenylphosphonium chloride. To a 40 ml glass vial were added 2.11 g of 80% cumene hydroperoxide, 0.4 g of the phase transfer catalyst, and a solution of 0.81 g of 85% KOH in 17.24 g of aqueous Methocel E50 solution followed by inserting a glass jacket housing a J type thermocouple and a homogenizer into the reaction mixture. The homogenizer was then turned on with the reaction vessel cooled with cold water. After the reaction mixture reached 21° C., addition of 2.18 g of 98% NDC started. After addition of NDC was finished, the reaction was then continued for additional ten minutes. During this period of time, the reaction temperature was maintained at or below 21° C. The reaction mixture was then analyzed with HPLC to determine the yield of CPN.

TABLE XII

| Example | 0.4 g of Agent | CHP:NDC:KOH | Yield of CPN (%) |
|---------|----------------|-------------|------------------|
| Control | N/A | 1:1.05:1.11 | 52.3 |
| 67 | TBAHS | 1:1.05:1.11 | 59.2 |
| 68 | CTMAC | 1:1.05:1.11 | 60.3 |
| 69 | Aliquat 175 | 1:1.05:1.11 | 70.6 |
| 70 | Aliquat 336 | 1:1.05:1.11 | 77.9 |
| 71 | Aliquat 100 | 1:1.05:1.11 | 73.2 |
| 72 | TBAB | 1:1.05:1.11 | 70.3 |
| 73 | TBAFTH | 1:1.05:1.11 | 69.8 |
| 74 | TPPB | 1:1.05:1.11 | 78.5 |
| 75 | TBPB | 1:1.05:1.11 | 78.2 |
| 76 | TPPC | 1:1.05:1.11 | 78.4 |

As illustrated by the Examples, the ammonium and phophonium salts can improve the CPN yield under the reaction conditions.

All patents and publications referred to herein are hereby incorporated by reference in their entireties.

Although the present invention and its advantages have been described in detail, it should be understood that various changes, substitutions, and alterations could be made herein without departing from the spirit and scope of the invention as defined by the appended claims.

We claim:

1. A process for the polymerization of at least one ethylenically unsaturated monomer comprising:
   (a) preparing a free radical initiator comprised of at least one organic peroxide, other than a peroxydicarbonate, selected from the group consisting of dialkyl peroxides and diacyl peroxides by forming a mixture of at least one inorganic peroxide and an aqueous emulsion of at least one organic halide wherein the emulsion is comprised of droplets of the organic halide with diameters of less than 10 μm and wherein the mixture reacts to form an aqueous emulsion of the at least one organic peroxide;
   (b) adding to a polymerization reactor at least one ethylenically unsaturated monomer;
   (c) adding to the polymerization reactor the aqueous emulsion of the at least one organic peroxide;
   (d) conducting a polymerization reaction to the desired level of conversion of said ethylenically unsaturated monomer to form a polymer;
   (e) discharging the polymer from the polymerization reactor; and
   (f) stripping said ethylenically unsaturated monomer from said polymer.

2. The process of claim 1 wherein said ethylenically unsaturated monomer is vinyl chloride monomer.

3. The process of claim 2 wherein the emulsion is comprised of droplets of at least one organic peroxide with diameters ranging from about 1 μm to about 4 μm.

4. The process of claim 3 wherein the emulsion of the at least one organic peroxide comprises at least two organic peroxides.

5. The process of claim 1 wherein the aqueous emulsion of the at least one organic peroxide is comprised of droplets of the at least one organic peroxide with diameters of less than 10 μm.

6. The process of claim 5 wherein the mixture of the at least one inorganic peroxide and the aqueous emulsion is formed by contacting the at least one inorganic peroxide and the at least one organic halide under conditions of agitation in the presence of a dispersant.

7. The process of claim 6 wherein the at least one dispersant is selected from the group consisting of hydrolyzed polyvinyl acetates, alkyl cellulose ethers, hydroxyalkyl cellulose ethers, gelatin, polyvinylpyrrolidone, polyoxyethlyene sorbitan monolaurate, polyacrylic acid and mixtures thereof.

8. The process of claim 5 wherein the mixture of the at least one inorganic peroxide and the aqueous emulsion is formed by subjecting the at least one organic halide to conditions of agitation in the presence of at least one dispersant to form an aqueous emulsion of the at least one organic halide comprised of droplets of the at least one organic halide having diameters of less than 10 μm and mixing the emulsion of the at least one organic halide with the at least one inorganic peroxide.

9. The process of claims 8 wherein the at least one dispersant is selected from the group consisting of hydrolyzed polyvinyl acetates, alkyl cellulose ethers, hydroxyalkyl cellulose ethers, gelatin, polyvinylpyrrolidone, polyoxyethlyene sorbitan monolaurate, polyacrylic acid and mixtures thereof.

10. The process of claim 9 wherein the mixture is formed in an in-line homogenizer.

11. The process of claim 10 wherein the process is continuous.

12. A process for the polymerization of at least one ethylenically unsaturated monomer comprising:
   (a) preparing a free radical initiator comprising at least one peroxyester by forming a mixture of at least one inorganic base and an aqueous emulsion of at least one organic hydroperoxide and at least one acylating agent comprised of droplets of the at least one organic hydroperoxide and the at least one acylating agent having diameters of less than 10 μm and wherein the mixture reacts to form an aqueous emulsion of the at least one peroxyester;
   (b) adding to a polymerization reactor at least one ethylenically unsaturated monomer;
   (c) adding to the polymerization reactor the aqueous emulsion of the at least one peroxyester;
   (d) conducting a polymerization reaction to the desired level of conversion of said ethylenically unsaturated monomer to form a polymer;
   (e) discharging the polymer from the polymerization reactor; and
   (f) stripping said ethylenically unsaturated monomer from said polymer.

13. The process of claim 12 wherein said ethylenically unsaturated monomer is vinyl chloride monomer.

14. The process of claim 13 wherein the emulsion is comprised of droplets of at least one organic peroxide with diameters ranging from about 1 μm to about 4 μm.

15. The process of claim 14 wherein the emulsion of the peroxyester comprises at least two organic peroxides.

16. The process of claim 15 wherein the aqueous emulsion of the at least one peroxyester is comprised of droplets of the at least one peroxyester with diameters of less than 10 μm.

17. The process of claim 16 wherein the mixture of the at least one inorganic base and the emulsion is formed by the process comprising the steps of:
   (a) contacting the at least one organic hydroperoxide and the at least one acylating agent under conditions of agitation in the presence of at least one dispersant to form an aqueous emulsion of the at least one organic hydroperoxide and the at least one acylating agent comprised of droplets of the at least one organic hydroperoxide and the at least one acylating agent having diameters of less than 10 µm and;

(b) mixing the emulsion of the at least one organic hydroperoxide and the at least one acylating agent with the at least one inorganic base.

18. The process of claim 17 wherein the at least one dispersant is selected from the group consisting of hydrolyzed polyvinyl acetates, alkyl cellulose ethers, hydroxyalkyl cellulose ethers, gelatin, polyvinylpyrrolidone, polyoxyethlyene sorbitan monolaurate, polyacrylic acid and mixtures thereof.

19. The process of claim 16 wherein the mixture of the at least one inorganic base and the emulsion of the emulsion of the at least one organic hydroperoxide and the at least one acylating agent is formed by the process comprising the steps of:

(a) contacting the at least one organic hydroperoxide and the at least one inorganic base under conditions of agitation in the presence of at least one dispersant to form a mixture of an emulsion of the at least one organic hydroperoxide comprised of droplets of the hydroperoxide having diameters less than 10 µm and the inorganic base and, (b) contacting the mixture of the emulsion of the at least one organic hydroperoxide and the inorganic base with the at least one acylating agent under conditions of agitation.

20. The process of claim 19 wherein the at least one dispersant is selected from the group consisting of hydrolyzed polyvinyl acetates, alkyl cellulose ethers, hydroxyalkyl cellulose ethers, gelatin, polyvinylpyrrolidone, polyoxyethlyene sorbitan monolaurate, polyacrylic acid and mixtures thereof.

21. The process of claim 20 wherein the mixture is formed in an in-line homogenizer.

22. The process of claim 21 wherein the process is continuous.

23. A process for the polymerization of at least one ethylenically unsaturated monomer comprising (a) preparing a free-radical initiator through the continuous production of a peroxydicarbonate by subjecting a stream of at least one haloformate to conditions of agitation in the presence of a dispersant to form an stream of an emulsion of the at least one haloformate comprised of droplets of the at least one haloformate having diameters of less than 10 µm and continuously blending a stream of a solution of at least one alkali metal peroxide into the stream of the emulsion of the at least one haloformate to form a stream comprised of an emulsion of the at least one peroxydicarbonate (b) adding to a polymerization reactor at least one ethylenically unsaturated monomer;

(c) adding to the polymerization reactor the emulsion of the at least one peroxydicarbonate (d) conducting a polymerization reaction to the desired level of conversion of the ethylenically unsaturated monomer to form a polymer;

(e) discharging said polymer from the polymerization reactor; and (f) stripping said ethylenically unsaturated monomer from said polymer.

24. The process of claim 23 wherein said ethylenically unsaturated monomer is vinyl chloride monomer.

25. The process of claim 24 wherein the emulsion is comprised of droplets of at least one peroxydicarbonate with diameters ranging from about 1 µm to about 4 µm.

26. The process of claim 25 wherein the at least one peroxydicarbonate is selected from the group consisting of di-ethyl peroxydicarbonate, n-propyl peroxydicarbonate, iso-propyl peroxydicarbonate, n-butyl peroxydicarbonate, s-butyl peroxydicarbonate, and 2-ethyl hexyl peroxydicarbonate.

27. The process of claim 26 wherein the emulsion of the at least one peroxydicarbonate comprises at least two different peroxydicarbonates.

28. A process for the polymerization of at least one ethylenically unsaturated monomer comprising:

(a) preparing a free radical initiator through the continuous production of a peroxydicarbonate by subjecting a stream of at least one haloformate to conditions of agitation in the presence of a dispersant to form an stream of an emulsion of the at least one haloformate comprised of droplets of the at least one haloformate having diameters of less than 10 µm and continuously blending a solution of hydrogen peroxide and a solution of at least one alkali metal hydroxide into the stream of the emulsion of the at least one haloformate to form a stream comprised of an emulsion of the at least one peroxydicarbonate;

(b) adding to a polymerization reactor at least one ethylenically unsaturated monomer;

(c) adding to the polymerization reactor the emulsion of the at least one peroxydicarbonate (d) conducting a polymerization reaction to the desired level of conversion of the ethylenically unsaturated monomer to form a polymer;

(e) discharging said polymer from the polymerization reactor; and (f) stripping said ethylenically unsaturated monomer from said polymer.

29. The process of claim 28 wherein said ethylenically unsaturated monomer is vinyl chloride monomer.

30. The process of claim 29 wherein the emulsion is comprised of droplets of at least one peroxydicarbonate with diameters ranging from about 1 µm to about 4 µm.

31. The process of claim 30 wherein the at least one peroxydicarbonate is selected from the group consisting of di-ethyl peroxydicarbonate, n-propyl peroxydicarbonate, iso-propyl peroxydicarbonate, n-butyl peroxydicarbonate, s-butyl peroxydicarbonate, and 2-ethyl hexyl peroxydicarbonate.

32. The process of claim 31 wherein the emulsion of the at least one peroxydicarbonate comprises at least two different peroxydicarbonates.

* * * * *